(12) United States Patent
Greenhalgh et al.

(10) Patent No.: US 10,758,289 B2
(45) Date of Patent: Sep. 1, 2020

(54) EXPANDABLE SUPPORT DEVICE AND METHOD OF USE

(71) Applicant: Stout Medical Group, L.P., Quakertown, PA (US)

(72) Inventors: E. Skott Greenhalgh, Gladwyne, PA (US); John-Paul Romano, Chalfont, PA (US)

(73) Assignee: Stout Medical Group, L.P., Warrington, PA (US)

( * ) Notice: Subject to any disclaimer, the term of this patent is extended or adjusted under 35 U.S.C. 154(b) by 0 days.

(21) Appl. No.: 14/882,300

(22) Filed: Oct. 13, 2015

(65) Prior Publication Data

US 2016/0030099 A1    Feb. 4, 2016

Related U.S. Application Data

(60) Continuation of application No. 13/216,123, filed on Aug. 23, 2011, now abandoned, which is a division of
(Continued)

(51) Int. Cl.
*A61B 17/70* (2006.01)
*A61B 17/88* (2006.01)

(52) U.S. Cl.
CPC ...... *A61B 17/8858* (2013.01); *A61B 17/7061* (2013.01); *A61B 17/7094* (2013.01); *A61B 17/7097* (2013.01); *A61B 17/7098* (2013.01)

(58) Field of Classification Search
CPC ............ A61B 17/8858; A61B 17/7094; A61B 17/7097; A61B 17/7098; A61B 17/844; A61B 17/7258; A61B 17/164; A61B 17/742; A61B 17/7275; A61B 17/1668; A61B 17/744; A61B 17/848; A61B 17/7291; A61B 17/8875; A61B 17/8685; A61B 17/863; A61B 17/866;
(Continued)

(56) References Cited

U.S. PATENT DOCUMENTS 646,119 A    3/1900   Clamer et al.
4,204,531 A  5/1980   Aginsky
(Continued)

FOREIGN PATENT DOCUMENTS

DE    19710392    7/1999
EP    0734702    10/1996
(Continued)

OTHER PUBLICATIONS

U.S. Appl. No. 11/689,465, filed Mar. 21, 2007.
(Continued)

*Primary Examiner* — Pedro Philogene
(74) *Attorney, Agent, or Firm* — Levine Bagade Han LLP

(57) ABSTRACT

An expandable support device for tissue repair is disclosed. The device can be used to repair hard or soft tissue, such as bone. The expandable support device can have interconnected struts. A method of repairing tissue is also disclosed. The expandable support device can be inserted into a damaged bone and radial expanded. The radial expansion of the expandable support device struts can cause the struts to cut mechanically support and/or the bone.

27 Claims, 27 Drawing Sheets

Related U.S. Application Data application No. 12/260,971, filed on Oct. 29, 2008, which is a continuation-in-part of application No. PCT/US2007/067967, filed on May 1, 2007.

(60) Provisional application No. 60/796,915, filed on May 1, 2006.

(58) Field of Classification Search
CPC .............. A61B 17/8872; A61B 17/861; A61B 17/8625; A61B 17/864; A61B 17/7073; A61F 2/4611; A61F 2/915; A61F 2/442; A61F 2/91
USPC .............. 606/62–68, 53, 99, 86 R, 313, 301; 623/17.11, 1.16, 11.16
See application file for complete search history.

(56) References Cited

U.S. PATENT DOCUMENTS

| | | |
|---|---|---|
| 4,541,423 A | 9/1985 | Barber |
| 4,569,338 A | 2/1986 | Edwards |
| 4,636,217 A | 1/1987 | Ogilvie et al. |
| 4,653,489 A | 3/1987 | Tronzo |
| 4,716,893 A | 1/1988 | Fischer et al. |
| 4,725,264 A | 2/1988 | Glassman |
| 4,733,665 A | 3/1988 | Palmaz |
| 4,759,769 A | 7/1988 | Hedman et al. |
| 4,763,644 A | 8/1988 | Webb |
| 4,863,476 A | 9/1989 | Shepperd |
| 4,886,062 A | 12/1989 | Wiktor |
| 4,911,718 A | 3/1990 | Lee et al. |
| 4,932,975 A | 6/1990 | Main et al. |
| 4,941,466 A | 7/1990 | Romano |
| 4,969,888 A | 11/1990 | Scholten et al. |
| 5,007,909 A | 4/1991 | Rogozinski |
| 5,015,247 A | 5/1991 | Michelson |
| 5,026,373 A | 6/1991 | Ray et al. |
| 5,059,193 A | 10/1991 | Kuslich |
| 5,108,404 A | 4/1992 | Scholten et al. |
| 5,123,926 A | 6/1992 | Pisharodi |
| 5,139,480 A | 8/1992 | Hickle et al. |
| 5,171,278 A | 12/1992 | Pisharodi |
| 5,192,327 A | 3/1993 | Brantigan |
| 5,217,483 A | 6/1993 | Tower |
| 5,258,031 A | 11/1993 | Salib et al. |
| 5,306,278 A | 4/1994 | Dahl et al. |
| 5,324,295 A | 6/1994 | Shapiro, III |
| 5,342,348 A | 8/1994 | Kaplan |
| 5,345,927 A | 9/1994 | Bonutti |
| 5,390,683 A | 2/1995 | Pisharodi |
| 5,390,898 A | 2/1995 | Smedley et al. |
| 5,397,364 A | 3/1995 | Kozak et al. |
| 5,425,773 A | 6/1995 | Boyd et al. |
| 5,454,365 A | 10/1995 | Bonutti |
| 5,458,643 A | 10/1995 | Oka et al. |
| 5,480,442 A | 1/1996 | Bertagnoli |
| 5,484,384 A | 1/1996 | Fearnot |
| 5,496,365 A | 3/1996 | Sgro |
| 5,522,899 A | 6/1996 | Michelson |
| 5,534,002 A | 7/1996 | Brumfield et al. |
| 5,540,690 A | 7/1996 | Miller et al. |
| 5,549,679 A | 8/1996 | Kuslich |
| 5,554,191 A | 9/1996 | Lahille et al. |
| 5,556,413 A | 9/1996 | Lam |
| 5,562,736 A | 10/1996 | Ray et al. |
| 5,562,738 A | 10/1996 | Boyd et al. |
| 5,571,189 A | 11/1996 | Kuslich |
| 5,571,192 A | 11/1996 | Schonhoffer |
| 5,584,831 A | 12/1996 | McKay |
| 5,591,197 A | 1/1997 | Orth et al. |
| 5,593,409 A | 1/1997 | Michelson |
| 5,609,356 A | 3/1997 | Mossi |
| 5,609,635 A | 3/1997 | Michelson |
| 5,643,264 A | 7/1997 | Sherman et al. |
| 5,643,312 A | 7/1997 | Fischell et al. |
| 5,645,560 A | 7/1997 | Crocker et al. |
| 5,649,950 A | 7/1997 | Bourne et al. |
| 5,653,763 A | 8/1997 | Errico et al. |
| 5,658,335 A | 8/1997 | Allen |
| 5,665,122 A | 9/1997 | Kambin |
| 5,669,909 A | 9/1997 | Zdeblick et al. |
| 5,674,295 A | 10/1997 | Ray et al. |
| 5,683,394 A | 11/1997 | Rinner |
| 5,693,100 A | 12/1997 | Pisharodi |
| 5,702,449 A | 12/1997 | Mckay |
| 5,702,453 A | 12/1997 | Rabbe et al. |
| 5,741,253 A | 4/1998 | Michelson |
| 5,749,916 A | 5/1998 | Richelsoph |
| 5,772,661 A | 6/1998 | Michelson |
| 5,776,181 A | 7/1998 | Lee et al. |
| 5,776,197 A | 7/1998 | Rabbe et al. |
| 5,776,198 A | 7/1998 | Rabbe et al. |
| 5,776,199 A | 7/1998 | Michelson |
| 5,782,832 A | 7/1998 | Larsen et al. |
| 5,782,903 A | 7/1998 | Wiktor |
| 5,785,710 A | 7/1998 | Michelson |
| 5,800,520 A | 9/1998 | Fogarty et al. |
| 5,824,054 A | 10/1998 | Khosravi et al. |
| 5,824,093 A | 10/1998 | Ray et al. |
| 5,827,289 A | 10/1998 | Reiley et al. |
| 5,827,321 A | 10/1998 | Roubin et al. |
| 5,853,419 A | 12/1998 | Imran |
| 5,861,025 A | 1/1999 | Boudghene et al. |
| 5,863,284 A | 1/1999 | Klein |
| 5,865,848 A | 2/1999 | Baker |
| 5,895,387 A | 4/1999 | Guerrero et al. |
| 5,902,475 A | 5/1999 | Trozera et al. |
| 5,972,015 A | 10/1999 | Scribner et al. |
| 5,980,522 A | 11/1999 | Koros et al. |
| 5,980,550 A | 11/1999 | Eder et al. |
| 5,984,957 A | 11/1999 | Laptewicz et al. |
| 5,993,483 A | 11/1999 | Gianotti |
| 6,001,130 A | 12/1999 | Bryan et al. |
| 6,019,765 A | 2/2000 | Thornhill et al. |
| 6,019,792 A | 2/2000 | Cauthen |
| 6,022,376 A | 2/2000 | Assell et al. |
| 6,025,104 A | 2/2000 | Fuller et al. |
| 6,027,527 A | 2/2000 | Asano et al. |
| 6,036,719 A | 3/2000 | Meilus |
| 6,039,761 A | 3/2000 | Li et al. |
| 6,045,579 A | 4/2000 | Hochshuler et al. |
| 6,053,916 A | 4/2000 | Moore |
| 6,066,154 A | 5/2000 | Reiley et al. |
| 6,077,246 A | 6/2000 | Kullas et al. |
| 6,080,158 A | 6/2000 | Lin |
| 6,080,193 A | 6/2000 | Hochshuler et al. |
| 6,083,522 A | 7/2000 | Chu et al. |
| 6,086,610 A | 7/2000 | Duerig et al. |
| 6,090,143 A | 7/2000 | Meriwether et al. |
| 6,102,619 A | 8/2000 | Truebe et al. |
| 6,102,950 A | 8/2000 | Vaccaro |
| 6,113,628 A | 9/2000 | Borghi |
| 6,113,639 A | 9/2000 | Ray et al. |
| 6,126,689 A | 10/2000 | Brett |
| 6,127,597 A | 10/2000 | Beyar et al. |
| 6,129,763 A | 10/2000 | Chauvin et al. |
| 6,132,465 A | 10/2000 | Ray et al. |
| 6,140,452 A | 10/2000 | Felt et al. |
| 6,146,417 A | 11/2000 | Ischinger |
| 6,159,244 A | 12/2000 | Suddaby |
| 6,159,245 A | 12/2000 | Meriwether et al. |
| 6,168,616 B1 | 1/2001 | Brown |
| 6,171,312 B1 | 1/2001 | Beaty |
| 6,176,882 B1 | 1/2001 | Biedermann et al. |
| 6,179,874 B1 | 1/2001 | Cauthen |
| 6,183,506 B1 | 2/2001 | Penn et al. |
| 6,183,517 B1 | 2/2001 | Suddaby |
| 6,193,757 B1 | 2/2001 | Foley et al. |
| 6,206,910 B1 | 3/2001 | Berry et al. |
| 6,206,924 B1 | 3/2001 | Timm |
| 6,224,595 B1 | 5/2001 | Michelson |
| 6,224,603 B1 | 5/2001 | Marino |
| 6,224,604 B1 | 5/2001 | Suddaby |

(56) References Cited

U.S. PATENT DOCUMENTS

| | | | |
|---|---|---|---|
| 6,224,607 B1 | 5/2001 | Michelson |
| 6,235,043 B1 | 5/2001 | Reiley et al. |
| 6,241,734 B1 | 6/2001 | Scribner et al. |
| 6,245,101 B1 | 6/2001 | Drasler et al. |
| 6,245,107 B1 | 6/2001 | Ferree |
| 6,248,110 B1 | 6/2001 | Reiley et al. |
| 6,280,456 B1 | 8/2001 | Scribner et al. |
| 6,287,332 B1 | 9/2001 | Bolz et al. |
| 6,293,967 B1 | 9/2001 | Shanley |
| 6,296,644 B1 | 10/2001 | Saurat et al. |
| 6,302,914 B1 | 10/2001 | Michelson |
| 6,332,895 B1 | 12/2001 | Suddaby |
| 6,371,989 B1 | 4/2002 | Chauvin et al. |
| 6,387,130 B1 | 5/2002 | Stone et al. |
| 6,395,031 B1 | 5/2002 | Foley et al. |
| 6,402,750 B1 | 6/2002 | Atkinson et al. |
| 6,402,785 B1 | 6/2002 | Zdeblick et al. |
| 6,409,765 B1 | 6/2002 | Bianchi et al. |
| 6,419,704 B1 | 7/2002 | Ferree |
| 6,419,705 B1 | 7/2002 | Erickson |
| 6,423,083 B2 | 7/2002 | Reiley et al. |
| 6,425,916 B1 | 7/2002 | Garrison et al. |
| 6,425,919 B1 | 7/2002 | Lambrecht |
| 6,428,569 B1 | 8/2002 | Brown |
| 6,432,107 B1 | 8/2002 | Ferree |
| 6,436,098 B1 | 8/2002 | Michelson |
| 6,436,140 B1 | 8/2002 | Liu et al. |
| 6,440,168 B1 | 8/2002 | Cauthen |
| 6,447,544 B1 | 9/2002 | Michelson |
| 6,447,546 B1 | 9/2002 | Bramlet et al. |
| 6,447,547 B1 | 9/2002 | Michelson |
| 6,451,025 B1 | 9/2002 | Jervis |
| 6,454,804 B1 | 9/2002 | Ferree |
| 6,468,301 B1 | 10/2002 | Amplatz et al. |
| 6,468,302 B2 | 10/2002 | Cox et al. |
| 6,475,237 B2 * | 11/2002 | Drasler .................... A61F 2/91 623/1.15 |
| 6,478,823 B1 | 11/2002 | Michelson |
| 6,482,235 B1 | 11/2002 | Lambrecht et al. |
| 6,488,710 B2 | 12/2002 | Besselink |
| 6,491,724 B1 | 12/2002 | Ferree |
| 6,494,883 B1 | 12/2002 | Ferree |
| 6,508,820 B2 | 1/2003 | Bales |
| 6,508,839 B1 | 1/2003 | Lambrecht et al. |
| 6,514,255 B1 | 2/2003 | Ferree |
| 6,520,991 B2 | 2/2003 | Huene |
| 6,533,817 B1 | 3/2003 | Norton et al. |
| 6,551,342 B1 | 4/2003 | Shen et al. |
| 6,554,833 B2 | 4/2003 | Levy et al. |
| 6,562,074 B2 | 5/2003 | Gerbec et al. |
| 6,582,431 B1 | 6/2003 | Ray |
| 6,582,467 B1 | 6/2003 | Teitelbaum et al. |
| 6,585,770 B1 | 7/2003 | White et al. |
| 6,592,589 B2 | 7/2003 | Hajianpour |
| 6,592,625 B2 | 7/2003 | Cauthen |
| 6,595,998 B2 | 7/2003 | Johnson et al. |
| 6,602,291 B1 | 8/2003 | Ray et al. |
| 6,607,530 B1 | 8/2003 | Carl et al. |
| 6,607,544 B1 | 8/2003 | Boucher et al. |
| 6,613,054 B2 | 9/2003 | Scribner et al. |
| 6,623,505 B2 | 9/2003 | Scribner et al. |
| 6,641,587 B2 | 11/2003 | Scribner et al. |
| 6,641,614 B1 | 11/2003 | Wagner et al. |
| 6,645,213 B2 | 11/2003 | Sand et al. |
| 6,645,247 B2 | 11/2003 | Ferree |
| 6,648,917 B2 | 11/2003 | Gerbec et al. |
| 6,648,918 B2 | 11/2003 | Ferree |
| 6,648,920 B2 | 11/2003 | Ferree |
| 6,652,584 B2 | 11/2003 | Michelson |
| 6,656,178 B1 | 12/2003 | Veldhuizen et al. |
| 6,663,647 B2 | 12/2003 | Reiley et al. |
| 6,666,891 B2 | 12/2003 | Boehm et al. |
| 6,676,665 B2 | 1/2004 | Foley et al. |
| 6,679,915 B1 | 1/2004 | Cauthen |
| 6,685,695 B2 | 2/2004 | Ferree |
| 6,695,760 B1 | 2/2004 | Winkler et al. |
| 6,706,068 B2 | 3/2004 | Ferree |
| 6,706,070 B1 | 3/2004 | Wagner et al. |
| 6,709,458 B2 | 3/2004 | Michelson |
| 6,712,853 B2 | 3/2004 | Kuslich |
| 6,716,216 B1 | 4/2004 | Boucher et al. |
| 6,716,247 B2 | 4/2004 | Michelson |
| 6,719,773 B1 | 4/2004 | Boucher et al. |
| 6,723,126 B1 | 4/2004 | Berry |
| 6,726,691 B2 | 4/2004 | Osorio et al. |
| 6,733,535 B2 | 5/2004 | Michelson |
| 6,736,818 B2 * | 5/2004 | Perren ................ A61B 17/7266 606/60 |
| 6,740,090 B1 | 5/2004 | Cragg et al. |
| 6,743,255 B2 | 6/2004 | Ferree |
| 6,746,451 B2 | 6/2004 | Middleton et al. |
| 6,758,863 B2 | 7/2004 | Estes et al. |
| 6,793,656 B1 | 9/2004 | Mathews |
| 6,793,679 B2 | 9/2004 | Michelson |
| 6,808,537 B2 | 10/2004 | Michelson |
| 6,814,756 B1 | 11/2004 | Michelson |
| 6,830,589 B2 | 12/2004 | Erickson |
| 6,852,115 B2 | 2/2005 | Kinnett |
| 6,852,123 B2 | 2/2005 | Brown |
| 6,852,129 B2 | 2/2005 | Gerbec et al. |
| 6,863,673 B2 | 3/2005 | Gerbec et al. |
| 6,893,464 B2 | 5/2005 | Kiester |
| 6,899,716 B2 | 5/2005 | Cragg |
| 6,899,719 B2 | 5/2005 | Reiley et al. |
| 6,921,264 B2 | 7/2005 | Mayer et al. |
| 6,923,813 B2 | 8/2005 | Phillips et al. |
| 6,923,830 B2 | 8/2005 | Michelson |
| 6,936,065 B2 | 8/2005 | Khan et al. |
| 6,936,070 B1 | 8/2005 | Muhanna |
| 6,948,223 B2 | 9/2005 | Shortt |
| 6,953,477 B2 | 10/2005 | Berry |
| 6,955,691 B2 | 10/2005 | Chae et al. |
| 6,960,215 B2 | 11/2005 | Olson et al. |
| 6,962,606 B2 | 11/2005 | Michelson |
| 6,981,981 B2 | 1/2006 | Reiley et al. |
| 6,988,710 B2 | 1/2006 | Igarashi |
| 7,008,453 B1 | 3/2006 | Michelson |
| 7,018,415 B1 | 3/2006 | McKay |
| 7,018,416 B2 | 3/2006 | Hanson et al. |
| 7,056,321 B2 | 6/2006 | Pagliuca et al. |
| 7,060,073 B2 | 6/2006 | Frey et al. |
| 7,066,961 B2 | 6/2006 | Michelson |
| 7,077,864 B2 | 7/2006 | Byrd et al. |
| 7,087,055 B2 | 8/2006 | Lim et al. |
| 7,094,257 B2 | 8/2006 | Mujwid et al. |
| 7,097,648 B1 | 8/2006 | Globerman et al. |
| 7,112,206 B2 | 9/2006 | Michelson |
| 7,118,598 B2 | 10/2006 | Michelson |
| 7,135,043 B2 | 11/2006 | Nakahara et al. |
| 7,166,110 B2 | 1/2007 | Yundt |
| 7,201,751 B2 | 4/2007 | Zucherman et al. |
| 7,201,775 B2 | 4/2007 | Gorensek et al. |
| 7,204,853 B2 | 4/2007 | Gordon et al. |
| 7,211,112 B2 | 5/2007 | Baynham et al. |
| 7,223,292 B2 | 5/2007 | Messerli et al. |
| 7,226,475 B2 | 6/2007 | Lenz et al. |
| 7,226,481 B2 | 6/2007 | Kuslich |
| 7,226,483 B2 | 6/2007 | Gerber et al. |
| 7,238,186 B2 | 7/2007 | Zdeblick et al. |
| 7,241,297 B2 | 7/2007 | Shaolian et al. |
| 7,241,303 B2 | 7/2007 | Reiss et al. |
| 7,300,440 B2 | 11/2007 | Zdeblick et al. |
| 7,309,338 B2 | 12/2007 | Cragg |
| 7,311,713 B2 | 12/2007 | Johnson et al. |
| 7,316,714 B2 | 1/2008 | Gordon et al. |
| 7,318,826 B2 | 1/2008 | Teitelbaum et al. |
| 7,396,360 B2 | 7/2008 | Lieberman |
| 7,431,735 B2 | 10/2008 | Liu et al. |
| 7,452,371 B2 | 11/2008 | Pavcnik et al. |
| 7,488,337 B2 | 2/2009 | Saab et al. |
| 7,503,933 B2 | 3/2009 | Michelson |
| 7,507,241 B2 | 3/2009 | Levy et al. |
| 7,582,106 B2 | 9/2009 | Teitelbaum et al. |
| 7,601,172 B2 | 10/2009 | Segal et al. |

(56) References Cited

U.S. PATENT DOCUMENTS

| | | |
|---|---|---|
| 7,618,457 B2 | 11/2009 | Hudgins |
| 7,621,950 B1 | 11/2009 | Globerman et al. |
| 7,625,395 B2 | 12/2009 | Mückter |
| 7,628,807 B2 * | 12/2009 | Flanagan .................. A61F 2/91 623/1.42 |
| 7,722,674 B1 | 5/2010 | Grotz |
| 7,749,228 B2 | 7/2010 | Lieberman |
| 7,763,028 B2 | 7/2010 | Lim et al. |
| 7,771,463 B2 | 8/2010 | Ton et al. |
| 7,828,849 B2 | 11/2010 | Lim |
| 7,837,734 B2 | 11/2010 | Zucherman et al. |
| 7,846,206 B2 | 12/2010 | Oglaza et al. |
| 7,867,233 B2 | 1/2011 | Shaolian et al. |
| 7,875,035 B2 | 1/2011 | Boucher et al. |
| 7,879,036 B2 | 2/2011 | Biedermann et al. |
| 7,879,082 B2 | 2/2011 | Brown |
| 8,007,498 B2 | 8/2011 | Mische |
| 8,034,110 B2 | 10/2011 | Garner et al. |
| 8,062,375 B2 | 11/2011 | Glerum et al. |
| 8,105,382 B2 | 1/2012 | Olmos et al. |
| 8,142,507 B2 | 3/2012 | McGuckin |
| 8,162,943 B2 | 4/2012 | Justin et al. |
| 8,206,423 B2 | 6/2012 | Siegal |
| 8,246,622 B2 | 8/2012 | Siegal et al. |
| 8,262,737 B2 | 9/2012 | Bagga et al. |
| 8,425,570 B2 | 4/2013 | Reiley |
| 8,465,524 B2 | 6/2013 | Siegal |
| 8,486,149 B2 | 7/2013 | Saidha et al. |
| 8,512,408 B2 | 8/2013 | Miller et al. |
| 8,518,120 B2 | 8/2013 | Glerum et al. |
| 8,535,380 B2 | 9/2013 | Greenhalgh et al. |
| 8,551,171 B2 | 10/2013 | Johnson et al. |
| 8,556,979 B2 | 10/2013 | Glerum et al. |
| 8,579,912 B2 | 11/2013 | Isaza et al. |
| 8,591,582 B2 | 11/2013 | Anderson et al. |
| 8,672,968 B2 | 3/2014 | Stone et al. |
| 8,672,977 B2 | 3/2014 | Siegal et al. |
| 8,679,183 B2 | 3/2014 | Glerum et al. |
| 8,685,098 B2 | 4/2014 | Glerum et al. |
| 8,709,042 B2 | 4/2014 | Greenhalgh et al. |
| 8,777,993 B2 | 7/2014 | Siegal et al. |
| 8,845,731 B2 | 9/2014 | Weiman |
| 8,845,734 B2 | 9/2014 | Weiman |
| 9,050,112 B2 | 6/2015 | Greenhalgh et al. |
| 9,149,286 B1 | 10/2015 | Greenhalgh et al. |
| 9,216,095 B2 | 12/2015 | Glerum et al. |
| 9,259,329 B2 | 2/2016 | Greenhalgh et al. |
| 9,314,349 B2 | 4/2016 | Greenhalgh et al. |
| 9,402,739 B2 | 8/2016 | Weiman et al. |
| 9,408,708 B2 | 8/2016 | Greenhalgh |
| 9,510,885 B2 | 12/2016 | Burger et al. |
| 9,770,339 B2 | 9/2017 | Greenhalgh et al. |
| 10,070,968 B2 | 9/2018 | Greenhalgh et al. |
| 10,285,819 B2 | 5/2019 | Greenhalgh |
| 10,285,820 B2 | 5/2019 | Greenhalgh |
| 10,292,828 B2 | 5/2019 | Greenhalgh |
| 2001/0007956 A1 | 7/2001 | Letac et al. |
| 2001/0034552 A1 | 10/2001 | Young et al. |
| 2002/0007218 A1 | 1/2002 | Cauthen |
| 2002/0010511 A1 | 1/2002 | Michelson |
| 2002/0022887 A1 | 2/2002 | Huene |
| 2002/0032444 A1 | 3/2002 | Mische |
| 2002/0038767 A1 | 4/2002 | Trozera |
| 2002/0052656 A1 | 5/2002 | Michelson |
| 2002/0068911 A1 | 6/2002 | Chan |
| 2002/0068939 A1 | 6/2002 | Levy et al. |
| 2002/0068975 A1 | 6/2002 | Teitelbaum et al. |
| 2002/0068976 A1 | 6/2002 | Jackson |
| 2002/0068977 A1 | 6/2002 | Jackson |
| 2002/0082598 A1 | 6/2002 | Teitelbaum |
| 2002/0082600 A1 | 6/2002 | Shaolian et al. |
| 2002/0091390 A1 | 7/2002 | Michelson |
| 2002/0095155 A1 | 7/2002 | Michelson |
| 2002/0099378 A1 | 7/2002 | Michelson |
| 2002/0111688 A1 | 8/2002 | Cauthen |
| 2002/0120337 A1 | 8/2002 | Cauthen |
| 2002/0123807 A1 | 9/2002 | Cauthen |
| 2002/0128713 A1 | 9/2002 | Ferree |
| 2002/0138077 A1 | 9/2002 | Ferree |
| 2002/0138133 A1 | 9/2002 | Lenz et al. |
| 2002/0138144 A1 | 9/2002 | Michelson |
| 2002/0143401 A1 | 10/2002 | Michelson |
| 2002/0151896 A1 | 10/2002 | Ferree |
| 2002/0151980 A1 | 10/2002 | Cauthen |
| 2002/0156530 A1 | 10/2002 | Lambrecht et al. |
| 2002/0161367 A1 | 10/2002 | Ferree |
| 2002/0161373 A1 | 10/2002 | Osorio et al. |
| 2002/0165542 A1 | 11/2002 | Ferree |
| 2002/0189622 A1 | 12/2002 | Cauthen et al. |
| 2002/0198526 A1 | 12/2002 | Shaolian et al. |
| 2003/0004511 A1 | 1/2003 | Ferree |
| 2003/0004574 A1 | 1/2003 | Ferree |
| 2003/0009227 A1 | 1/2003 | Lambrecht et al. |
| 2003/0014118 A1 | 1/2003 | Lambrecht et al. |
| 2003/0026788 A1 | 2/2003 | Ferree |
| 2003/0032963 A1 | 2/2003 | Reiss et al. |
| 2003/0040796 A1 | 2/2003 | Ferree |
| 2003/0040798 A1 | 2/2003 | Michelson |
| 2003/0050701 A1 | 3/2003 | Michelson |
| 2003/0065394 A1 | 4/2003 | Michelson |
| 2003/0065396 A1 | 4/2003 | Michelson |
| 2003/0074076 A1 | 4/2003 | Ferree et al. |
| 2003/0078579 A1 | 4/2003 | Ferree |
| 2003/0088249 A1 | 5/2003 | Furderer |
| 2003/0120345 A1 | 6/2003 | Cauthen |
| 2003/0125748 A1 | 7/2003 | Li et al. |
| 2003/0125807 A1 | 7/2003 | Lambrecht et al. |
| 2003/0135220 A1 | 7/2003 | Cauthen |
| 2003/0135279 A1 | 7/2003 | Michelson |
| 2003/0149482 A1 | 8/2003 | Michelson |
| 2003/0153976 A1 | 8/2003 | Cauthen et al. |
| 2003/0158553 A1 | 8/2003 | Michelson |
| 2003/0158604 A1 | 8/2003 | Cauthen et al. |
| 2003/0163200 A1 | 8/2003 | Cauthen |
| 2003/0171813 A1 | 9/2003 | Kiester |
| 2003/0181979 A1 | 9/2003 | Ferree |
| 2003/0181980 A1 | 9/2003 | Berry et al. |
| 2003/0181983 A1 | 9/2003 | Cauthen |
| 2003/0187507 A1 | 10/2003 | Cauthen |
| 2003/0187508 A1 | 10/2003 | Cauthen |
| 2003/0191536 A1 | 10/2003 | Ferree |
| 2003/0195514 A1 | 10/2003 | Trieu et al. |
| 2003/0195630 A1 | 10/2003 | Ferree |
| 2003/0195631 A1 | 10/2003 | Ferree |
| 2003/0199979 A1 | 10/2003 | Mcguckin |
| 2003/0199981 A1 | 10/2003 | Ferree |
| 2003/0204189 A1 | 10/2003 | Cragg |
| 2003/0204260 A1 | 10/2003 | Ferree |
| 2003/0208270 A9 | 11/2003 | Michelson |
| 2003/0220643 A1 | 11/2003 | Ferree |
| 2003/0220650 A1 | 11/2003 | Major et al. |
| 2003/0220690 A1 | 11/2003 | Cauthen |
| 2003/0220693 A1 | 11/2003 | Cauthen |
| 2003/0220694 A1 | 11/2003 | Cauthen |
| 2003/0233097 A1 | 12/2003 | Ferree |
| 2003/0233148 A1 | 12/2003 | Ferree |
| 2003/0236520 A1 | 12/2003 | Lim et al. |
| 2004/0002759 A1 | 1/2004 | Ferree |
| 2004/0002760 A1 | 1/2004 | Boyd et al. |
| 2004/0002769 A1 | 1/2004 | Ferree |
| 2004/0006341 A1 | 1/2004 | Shaolian et al. |
| 2004/0006344 A1 | 1/2004 | Nguyen et al. |
| 2004/0010315 A1 | 1/2004 | Song |
| 2004/0010318 A1 | 1/2004 | Ferree |
| 2004/0019386 A1 | 1/2004 | Ferree |
| 2004/0024400 A1 | 2/2004 | Michelson |
| 2004/0024459 A1 | 2/2004 | Ferree |
| 2004/0024460 A1 | 2/2004 | Ferree |
| 2004/0024461 A1 | 2/2004 | Ferree |
| 2004/0024462 A1 | 2/2004 | Ferree et al. |
| 2004/0024469 A1 | 2/2004 | Ferree |
| 2004/0024471 A1 | 2/2004 | Ferree |
| 2004/0028718 A1 | 2/2004 | Ferree |
| 2004/0030387 A1 | 2/2004 | Landry et al. |

(56) References Cited

U.S. PATENT DOCUMENTS

| | | |
|---|---|---|
| 2004/0030389 A1 | 2/2004 | Ferree |
| 2004/0030390 A1 | 2/2004 | Ferree |
| 2004/0030391 A1 | 2/2004 | Ferree |
| 2004/0030398 A1 | 2/2004 | Ferree |
| 2004/0034357 A1 | 2/2004 | Beane et al. |
| 2004/0044410 A1 | 3/2004 | Ferree et al. |
| 2004/0049289 A1 | 3/2004 | Tordy et al. |
| 2004/0059418 A1 | 3/2004 | Mckay et al. |
| 2004/0059419 A1 | 3/2004 | Michelson |
| 2004/0059429 A1 | 3/2004 | Amin et al. |
| 2004/0068259 A1 | 4/2004 | Michelson |
| 2004/0082954 A1 | 4/2004 | Teitelbaum et al. |
| 2004/0082961 A1 | 4/2004 | Teitelbaum |
| 2004/0087947 A1 | 5/2004 | Lim et al. |
| 2004/0087950 A1 | 5/2004 | Teitelbaum |
| 2004/0092933 A1 | 5/2004 | Shaolian et al. |
| 2004/0092946 A1 | 5/2004 | Bagga et al. |
| 2004/0092988 A1 | 5/2004 | Shaolian et al. |
| 2004/0097927 A1 | 5/2004 | Yeung et al. |
| 2004/0102848 A1 | 5/2004 | Michelson |
| 2004/0111108 A1 | 6/2004 | Farnan |
| 2004/0133229 A1 | 7/2004 | Lambrecht et al. |
| 2004/0133280 A1 | 7/2004 | Trieu |
| 2004/0138673 A1 | 7/2004 | Lambrecht et al. |
| 2004/0153064 A1 | 8/2004 | Foley et al. |
| 2004/0153065 A1 | 8/2004 | Lim |
| 2004/0153146 A1 | 8/2004 | Lashinski et al. |
| 2004/0167625 A1 | 8/2004 | Beyar et al. |
| 2004/0172019 A1 | 9/2004 | Ferree |
| 2005/0010292 A1 | 1/2005 | Carrasco |
| 2005/0015152 A1 | 1/2005 | Sweeney |
| 2005/0022839 A1 | 2/2005 | Savas et al. |
| 2005/0033431 A1 | 2/2005 | Gordon et al. |
| 2005/0038512 A1 | 2/2005 | Michelson |
| 2005/0043796 A1 | 2/2005 | Grant et al. |
| 2005/0070911 A1 | 3/2005 | Carrison et al. |
| 2005/0080422 A1 | 4/2005 | Otte et al. |
| 2005/0085910 A1 | 4/2005 | Sweeney |
| 2005/0107863 A1 | 5/2005 | Brown |
| 2005/0113919 A1 | 5/2005 | Cragg et al. |
| 2005/0113928 A1 | 5/2005 | Cragg et al. |
| 2005/0119561 A1 | 6/2005 | Kienzle |
| 2005/0143827 A1 | 6/2005 | Globerman et al. |
| 2005/0182463 A1 | 8/2005 | Hunter et al. |
| 2005/0187558 A1 | 8/2005 | Johnson et al. |
| 2005/0209698 A1 | 9/2005 | Gordon et al. |
| 2005/0228391 A1 | 10/2005 | Levy et al. |
| 2005/0228472 A1 | 10/2005 | Case et al. |
| 2005/0240188 A1 | 10/2005 | Chow et al. |
| 2005/0249776 A1 | 11/2005 | Chen et al. |
| 2005/0261683 A1 | 11/2005 | Veldhuizen et al. |
| 2005/0261695 A1 | 11/2005 | Cragg et al. |
| 2005/0261768 A1 | 11/2005 | Trieu |
| 2005/0261781 A1* | 11/2005 | Sennett ............ A61B 17/7098 623/23.54 |
| 2005/0278023 A1 | 12/2005 | Zwirkoski |
| 2005/0278026 A1 | 12/2005 | Gordon et al. |
| 2005/0278036 A1 | 12/2005 | Leonard et al. |
| 2006/0004455 A1 | 1/2006 | Leonard et al. |
| 2006/0015184 A1 | 1/2006 | Winterbottom et al. |
| 2006/0022180 A1 | 2/2006 | Selness |
| 2006/0036241 A1 | 2/2006 | Siegal |
| 2006/0036273 A1 | 2/2006 | Siegal |
| 2006/0052788 A1 | 3/2006 | Thelen et al. |
| 2006/0052870 A1 | 3/2006 | Ferree |
| 2006/0058807 A1 | 3/2006 | Landry et al. |
| 2006/0058876 A1 | 3/2006 | Mckinley |
| 2006/0058880 A1 | 3/2006 | Wysocki et al. |
| 2006/0079898 A1 | 4/2006 | Ainsworth et al. |
| 2006/0085069 A1 | 4/2006 | Kim |
| 2006/0085070 A1* | 4/2006 | Kim ................ A61B 17/7065 623/17.11 |
| 2006/0089715 A1 | 4/2006 | Truckai et al. |
| 2006/0095123 A1 | 5/2006 | Flanagan |
| 2006/0100706 A1 | 5/2006 | Shadduck et al. |
| 2006/0106460 A1 | 5/2006 | Messerli et al. |
| 2006/0122701 A1 | 6/2006 | Kiester |
| 2006/0129244 A1 | 6/2006 | Ensign |
| 2006/0142858 A1 | 6/2006 | Colleran et al. |
| 2006/0142859 A1 | 6/2006 | Mcluen |
| 2006/0149239 A1 | 7/2006 | Winslow et al. |
| 2006/0149349 A1 | 7/2006 | Garbe |
| 2006/0149385 A1 | 7/2006 | Mckay |
| 2006/0155379 A1 | 7/2006 | Heneveld et al. |
| 2006/0161261 A1 | 7/2006 | Brown et al. |
| 2006/0178694 A1 | 8/2006 | Greenhalgh et al. |
| 2006/0184188 A1 | 8/2006 | Li et al. |
| 2006/0184248 A1 | 8/2006 | Edidin et al. |
| 2006/0189999 A1 | 8/2006 | Zwirkoski |
| 2006/0200166 A1 | 9/2006 | Hanson et al. |
| 2006/0206207 A1 | 9/2006 | Dryer et al. |
| 2006/0235414 A1 | 10/2006 | Lim et al. |
| 2006/0235423 A1 | 10/2006 | Cantu |
| 2006/0241764 A1 | 10/2006 | Michelson |
| 2006/0253201 A1 | 11/2006 | Mcluen |
| 2006/0264968 A1 | 11/2006 | Frey et al. |
| 2006/0265077 A1 | 11/2006 | Zwirkoski |
| 2006/0271061 A1 | 11/2006 | Beyar et al. |
| 2006/0287725 A1 | 12/2006 | Miller |
| 2006/0287726 A1 | 12/2006 | Segal et al. |
| 2006/0287727 A1 | 12/2006 | Segal et al. |
| 2006/0287729 A1 | 12/2006 | Segal et al. |
| 2006/0287730 A1 | 12/2006 | Segal et al. |
| 2007/0027363 A1 | 2/2007 | Gannoe et al. |
| 2007/0032791 A1 | 2/2007 | Greenhalgh |
| 2007/0043440 A1* | 2/2007 | William ............ A61B 17/8858 623/17.11 |
| 2007/0055201 A1 | 3/2007 | Seto et al. |
| 2007/0055375 A1 | 3/2007 | Ferree |
| 2007/0055377 A1 | 3/2007 | Hanson et al. |
| 2007/0067034 A1* | 3/2007 | Chirico ................ A61B 17/70 623/17.11 |
| 2007/0067035 A1 | 3/2007 | Falahee |
| 2007/0093897 A1 | 4/2007 | Gerbec et al. |
| 2007/0093899 A1 | 4/2007 | Dutoit et al. |
| 2007/0112428 A1 | 5/2007 | Lancial |
| 2007/0118222 A1 | 5/2007 | Lang |
| 2007/0123877 A1 | 5/2007 | Goldin et al. |
| 2007/0123986 A1 | 5/2007 | Schaller |
| 2007/0162044 A1 | 7/2007 | Marino |
| 2007/0162135 A1 | 7/2007 | Segal et al. |
| 2007/0173824 A1 | 7/2007 | Rosen |
| 2007/0173830 A1 | 7/2007 | Rosen |
| 2007/0173939 A1* | 7/2007 | Kim ................ A61B 17/1633 623/17.11 |
| 2007/0173940 A1 | 7/2007 | Hestad et al. |
| 2007/0208423 A1 | 9/2007 | Messerli et al. |
| 2007/0213717 A1 | 9/2007 | Trieu et al. |
| 2007/0219634 A1 | 9/2007 | Greenhalgh et al. |
| 2007/0225703 A1 | 9/2007 | Schmitz et al. |
| 2007/0233260 A1 | 10/2007 | Cragg |
| 2007/0239162 A1 | 10/2007 | Bhatnagar et al. |
| 2007/0244485 A1 | 10/2007 | Greenhalgh et al. |
| 2007/0255408 A1 | 11/2007 | Castleman et al. |
| 2007/0255409 A1 | 11/2007 | Dickson et al. |
| 2007/0260270 A1 | 11/2007 | Assell et al. |
| 2007/0260315 A1 | 11/2007 | Foley et al. |
| 2007/0270956 A1 | 11/2007 | Heinz |
| 2007/0270968 A1 | 11/2007 | Baynham et al. |
| 2007/0276377 A1 | 11/2007 | Yundt |
| 2007/0276382 A1 | 11/2007 | Mikhail et al. |
| 2007/0282342 A1 | 12/2007 | Niederberger et al. |
| 2007/0288028 A1 | 12/2007 | Gorensek et al. |
| 2008/0015694 A1 | 1/2008 | Tribus |
| 2008/0021558 A1 | 1/2008 | Thramann |
| 2008/0021559 A1 | 1/2008 | Thramann |
| 2008/0071356 A1 | 3/2008 | Greenhalgh et al. |
| 2008/0077150 A1 | 3/2008 | Nguyen |
| 2008/0082162 A1 | 4/2008 | Boismier et al. |
| 2008/0124865 A1 | 5/2008 | Lutze et al. |
| 2008/0125864 A1 | 5/2008 | De Villiers et al. |
| 2008/0125865 A1 | 5/2008 | Abdelgany |
| 2008/0133012 A1 | 6/2008 | McGuckin |
| 2008/0140082 A1 | 6/2008 | Erdem et al. |

(56) References Cited

U.S. PATENT DOCUMENTS

| | | | |
|---|---|---|---|
| 2008/0140179 A1* | 6/2008 | Ladisa | A61F 2/91 623/1.11 |
| 2008/0140207 A1 | 6/2008 | Olmos et al. | |
| 2008/0147193 A1 | 6/2008 | Matthis et al. | |
| 2008/0147194 A1 | 6/2008 | Grotz et al. | |
| 2008/0183204 A1 | 7/2008 | Greenhalgh et al. | |
| 2008/0188941 A1 | 8/2008 | Grotz | |
| 2008/0208255 A1 | 8/2008 | Siegal | |
| 2008/0221687 A1 | 9/2008 | Viker | |
| 2008/0243254 A1 | 10/2008 | Butler | |
| 2008/0243255 A1 | 10/2008 | Butler et al. | |
| 2008/0249625 A1 | 10/2008 | Waugh et al. | |
| 2008/0249628 A1 | 10/2008 | Altarac et al. | |
| 2008/0281346 A1 | 11/2008 | Greenhalgh et al. | |
| 2008/0294205 A1 | 11/2008 | Greenhalgh et al. | |
| 2008/0312743 A1 | 12/2008 | Vila et al. | |
| 2008/0312744 A1 | 12/2008 | Vresilovic et al. | |
| 2009/0005871 A1 | 1/2009 | White et al. | |
| 2009/0012564 A1 | 1/2009 | Chirico et al. | |
| 2009/0018524 A1 | 1/2009 | Greenhalgh et al. | |
| 2009/0024204 A1 | 1/2009 | Greenhalgh et al. | |
| 2009/0024217 A1 | 1/2009 | Levy et al. | |
| 2009/0054991 A1 | 2/2009 | Biyani et al. | |
| 2009/0076511 A1 | 3/2009 | Osman | |
| 2009/0143859 A1 | 6/2009 | McClellan et al. | |
| 2009/0149956 A1 | 6/2009 | Greenhalgh et al. | |
| 2009/0163918 A1 | 6/2009 | Levy et al. | |
| 2009/0177207 A1 | 7/2009 | Schaller | |
| 2009/0182336 A1 | 7/2009 | Brenzel et al. | |
| 2009/0182431 A1 | 7/2009 | Butler et al. | |
| 2009/0198338 A1 | 8/2009 | Phan | |
| 2009/0234398 A1 | 9/2009 | Chirico et al. | |
| 2009/0240335 A1 | 9/2009 | Arcenio et al. | |
| 2009/0292323 A1 | 11/2009 | Chirico et al. | |
| 2009/0299378 A1 | 12/2009 | Knopp | |
| 2009/0318928 A1 | 12/2009 | Purcell et al. | |
| 2010/0004750 A1 | 1/2010 | Segal et al. | |
| 2010/0004751 A1 | 1/2010 | Segal et al. | |
| 2010/0016905 A1 | 1/2010 | Greenhalgh et al. | |
| 2010/0082109 A1 | 4/2010 | Greenhalgh et al. | |
| 2010/0125274 A1 | 5/2010 | Greenhalgh et al. | |
| 2010/0168748 A1 | 7/2010 | Knopp et al. | |
| 2010/0168862 A1 | 7/2010 | Edie et al. | |
| 2010/0191336 A1 | 7/2010 | Greenhalgh | |
| 2010/0211176 A1 | 8/2010 | Greenhalgh | |
| 2010/0262147 A1 | 10/2010 | Siegal et al. | |
| 2010/0292796 A1 | 11/2010 | Greenhalgh et al. | |
| 2010/0324560 A1 | 12/2010 | Suda | |
| 2011/0009869 A1 | 1/2011 | Marino et al. | |
| 2011/0009969 A1 | 1/2011 | Puno | |
| 2011/0029083 A1 | 2/2011 | Hynes et al. | |
| 2011/0046737 A1 | 2/2011 | Teisen | |
| 2011/0054621 A1 | 3/2011 | Lim | |
| 2011/0087296 A1 | 4/2011 | Reiley et al. | |
| 2011/0106260 A1 | 5/2011 | Laurence et al. | |
| 2011/0118785 A1 | 5/2011 | Reiley | |
| 2011/0125266 A1 | 5/2011 | Rodgers et al. | |
| 2011/0153019 A1 | 6/2011 | Siegal | |
| 2011/0166575 A1 | 7/2011 | Assell et al. | |
| 2011/0184519 A1 | 7/2011 | Trieu | |
| 2011/0218626 A1* | 9/2011 | Krinke | A61F 2/28 623/16.11 |
| 2011/0230884 A1 | 9/2011 | Mantzaris et al. | |
| 2011/0230966 A1 | 9/2011 | Trieu | |
| 2011/0257684 A1 | 10/2011 | Sankaran | |
| 2011/0282387 A1 | 11/2011 | Suh et al. | |
| 2011/0282398 A1 | 11/2011 | Overes et al. | |
| 2011/0282453 A1 | 11/2011 | Greenhalgh et al. | |
| 2011/0319898 A1 | 12/2011 | O'Neil et al. | |
| 2011/0320000 A1 | 12/2011 | O'Neil et al. | |
| 2012/0004726 A1 | 1/2012 | Greenhalgh et al. | |
| 2012/0004731 A1 | 1/2012 | Viker | |
| 2012/0029518 A1 | 2/2012 | Blackwell et al. | |
| 2012/0071962 A1 | 3/2012 | Huang et al. | |
| 2012/0071980 A1 | 3/2012 | Purcell et al. | |
| 2013/0035723 A1 | 2/2013 | Donner | |
| 2013/0053852 A1 | 2/2013 | Greenhalgh et al. | |
| 2013/0085535 A1 | 4/2013 | Greenhalgh et al. | |
| 2013/0138214 A1 | 5/2013 | Greenhalgh et al. | |
| 2013/0173004 A1 | 7/2013 | Greenhalgh et al. | |
| 2013/0304224 A1 | 11/2013 | Schmidt et al. | |
| 2014/0088713 A1 | 3/2014 | Greenhalgh et al. | |
| 2014/0155980 A1 | 6/2014 | Turjman et al. | |
| 2015/0230931 A1 | 8/2015 | Greenhalgh | |
| 2015/0265417 A1 | 9/2015 | Greenhalgh et al. | |
| 2015/0351930 A1 | 12/2015 | Greenhalgh et al. | |
| 2016/0022429 A1 | 1/2016 | Greenhalgh et al. | |
| 2016/0058572 A1 | 3/2016 | Greenhalgh et al. | |
| 2016/0310291 A1 | 10/2016 | Greenhalgh | |
| 2016/0374727 A1 | 12/2016 | Greenhalgh et al. | |
| 2017/0119540 A1 | 5/2017 | Greenhalgh | |
| 2017/0119541 A1 | 5/2017 | Greenhalgh | |
| 2017/0165083 A1 | 6/2017 | Greenhalgh | |
| 2017/0181865 A1 | 6/2017 | Greenhalgh et al. | |
| 2017/0196613 A1 | 7/2017 | Greenhalgh et al. | |
| 2017/0319353 A1 | 11/2017 | Greenhalgh et al. | |
| 2017/0348115 A1 | 12/2017 | Greenhalgh et al. | |
| 2018/0256359 A1 | 9/2018 | Greenhalgh | |
| 2018/0368986 A1 | 12/2018 | Greenhalgh et al. | |
| 2019/0231549 A1 | 8/2019 | Greenhalgh et al. | |
| 2019/0240043 A1 | 8/2019 | Greenhalgh | |
| 2019/0254714 A1 | 8/2019 | Greenhalgh et al. | |

FOREIGN PATENT DOCUMENTS

| | | |
|---|---|---|
| EP | 0758541 | 2/1997 |
| EP | 1804733 | 7/2007 |
| FR | 2874814 | 11/2007 |
| FR | 2900814 | 11/2007 |
| JP | 2000-210315 | 8/2000 |
| JP | 2002-535080 | 10/2002 |
| JP | 2003-512887 | 4/2003 |
| JP | 2004-511297 | 4/2004 |
| JP | 2004-531355 | 10/2004 |
| JP | 2004-321348 | 11/2004 |
| JP | 2012-522961 | 9/2012 |
| SU | 662082 | 5/1979 |
| WO | WO 1988/003781 | 6/1988 |
| WO | WO 1992/014423 | 9/1992 |
| WO | WO 1995/031945 | 11/1995 |
| WO | WO 1996/003092 | 2/1996 |
| WO | WO 1997/000054 | 1/1997 |
| WO | WO 2000/025706 | 5/2000 |
| WO | WO 2000/030523 | 6/2000 |
| WO | WO 2000/044319 | 8/2000 |
| WO | WO 2000/044321 | 8/2000 |
| WO | WO 2001/032099 | 5/2001 |
| WO | WO 2001/078625 | 10/2001 |
| WO | WO 2001/095838 | 12/2001 |
| WO | WO 2002/013700 | 2/2002 |
| WO | WO 2002/032347 | 4/2002 |
| WO | WO 2003/003943 | 1/2003 |
| WO | WO 2003/003951 | 1/2003 |
| WO | WO 2005/062900 | 7/2005 |
| WO | WO 2005/096975 | 10/2005 |
| WO | WO 2005/120400 | 12/2005 |
| WO | WO 2006/023514 | 3/2006 |
| WO | WO 2006/023671 | 3/2006 |
| WO | WO 2006/026425 | 3/2006 |
| WO | WO 2006/028971 | 3/2006 |
| WO | WO 2006/034396 | 3/2006 |
| WO | WO 2006/034436 | 3/2006 |
| WO | WO 2006/037013 | 4/2006 |
| WO | WO 2006/042334 | 4/2006 |
| WO | WO 2006/050500 | 5/2006 |
| WO | WO 2006/060420 | 6/2006 |
| WO | WO 2006/068682 | 6/2006 |
| WO | WO 2006/072941 | 7/2006 |
| WO | WO 2006/076712 | 7/2006 |
| WO | WO 2006/086241 | 8/2006 |
| WO | WO 2006/096167 | 9/2006 |
| WO | WO 2006/116760 | 11/2006 |
| WO | WO 2006/116761 | 11/2006 |
| WO | WO 2006/132945 | 12/2006 |

(56) References Cited

FOREIGN PATENT DOCUMENTS

| | | |
|---|---|---|
| WO | WO 2007/009107 | 1/2007 |
| WO | WO 2007/009123 | 1/2007 |
| WO | WO 2007/016368 | 2/2007 |
| WO | WO 2007/038611 | 4/2007 |
| WO | WO 2007/041665 | 4/2007 |
| WO | WO 2007/041698 | 4/2007 |
| WO | WO 2007/047098 | 4/2007 |
| WO | WO 2007/050322 | 5/2007 |
| WO | WO 2007/056433 | 5/2007 |
| WO | WO 2007/062080 | 5/2007 |
| WO | WO 2007/073488 | 6/2007 |
| WO | WO 2007/075411 | 7/2007 |
| WO | WO 2007/076308 | 7/2007 |
| WO | WO 2007/076374 | 7/2007 |
| WO | WO 2007/076376 | 7/2007 |
| WO | WO 2007/076377 | 7/2007 |
| WO | WO 2007/079021 | 7/2007 |
| WO | WO 2007/084239 | 7/2007 |
| WO | WO 2007/084257 | 7/2007 |
| WO | WO 2007/084268 | 7/2007 |
| WO | WO 2007/084810 | 7/2007 |
| WO | WO 2007/100591 | 9/2007 |
| WO | WO 2007/113808 | 10/2007 |
| WO | WO 2007/123920 | 11/2007 |
| WO | WO 2007/124130 | 11/2007 |
| WO | WO 2007/126622 | 11/2007 |
| WO | WO 2007/130699 | 11/2007 |
| WO | WO 2007/131026 | 11/2007 |
| WO | WO 2007/133608 | 11/2007 |
| WO | WO 2007/140382 | 12/2007 |
| WO | WO 2008/005627 | 1/2008 |
| WO | WO 2008/016598 | 2/2008 |
| WO | WO 2008/036505 | 3/2008 |
| WO | WO 2008/070863 | 6/2008 |
| WO | WO 2009/039430 | 3/2009 |
| WO | WO 2009/067568 | 5/2009 |
| WO | WO 2009/114381 | 9/2009 |
| WO | WO 2009/130824 | 10/2009 |
| WO | WO 2010/013188 | 2/2010 |
| WO | WO 2010/121002 | 10/2010 |
| WO | WO 2011/014502 | 2/2011 |
| WO | WO 2011/049949 | 4/2011 |
| WO | WO 2011/142761 | 11/2011 |
| WO | WO 2011/149557 | 12/2011 |
| WO | WO 2012/027490 | 3/2012 |
| WO | WO 2012/040272 | 3/2012 |
| WO | WO 2012/083173 | 6/2012 |
| WO | WO 2013/028808 | 2/2013 |
| WO | WO 2013/119332 | 8/2013 |

OTHER PUBLICATIONS

U.S. Appl. No. 11/689,471, filed Mar. 21, 2007.
U.S. Appl. No. 14/085,563, filed Nov. 20, 2013.
U.S. Appl. No. 12/098,297, filed Apr. 4, 2008.
U.S. Appl. No. 12/139,367, filed Jun. 13, 2008.
U.S. Appl. No. 12/693,382, filed Jan. 25, 2010.
U.S. Appl. No. 11/877,610, filed Oct. 23, 2007.
U.S. Appl. No. 11/457,772, filed July 14, 2006.
U.S. Appl. No. 12/014,006, filed Jan. 14, 2008.
U.S. Appl. No. 12/139,396, filed Jun. 13, 2008.
U.S. Appl. No. 12/139,406, filed Jun. 13, 2008.
U.S. Appl. No. 12/260,971, filed Oct. 29, 2008.
U.S. Appl. No. 13/216,123, filed Aug. 23, 2011.
U.S. Appl. No. 12/564,616, filed Sep. 22, 2009.
U.S. Appl. No. 12/693,394, filed Jan. 25, 2010.
U.S. Appl. No. 12/694,221, filed Jan. 26, 2010.
U.S. Appl. No. 12/779,865, filed May 13, 2010.
U.S. Appl. No. 14/703,704, filed May 4, 2015.
U.S. Appl. No. 13/686,775, filed Nov. 27, 2012.
U.S. Appl. No. 13/773,100, filed Febr. 21, 2013.
U.S. Appl. No. 14/874,150, filed Oct. 2, 2015.
U.S. Appl. No. 13/573,542, filed Sep. 21, 2012.
U.S. Appl. No. 13/296,066, filed Nov. 14, 2011.
U.S. Appl. No. 14/796,898, filed Jul. 10, 2015
U.S. Appl. No. 13/592,271, filed Aug. 22, 2012.
Choi, G. et al., "Percutaneous Endoscopic Lumbar Discemtomy by Transiliac Approach," *Spine*, 34(12):E443-446, May 20, 2009.
Database WPI, Week 198004, Thomson Scientific, London, GB; AN 1980-A8866C, XP002690114, -& SU 662 082 A1 (Tartus Univ) May 15, 1979 (May 15, 1979), abstract, figures 1,2.
Franklin, I.J. et al., "Uptake of Tetracycline by Aortic Aneurysm Wall and Its Effect on Inflammation and Proteolysis," *Brit. J. Surger*, 86(6):771-775, 1999.
Pyo, R. et al., "Targeted Gene Disruption of Matrix Metalloproteinase-9 (Gelatinase B) Suppresses Development of Experimental Abdominal Aortic Aneurysms," *J. Clinical Inyestigation*,105(11):1641-1649, Jun. 2000.
Tambiah, J. et al., "Provocation of Experimental Aortic Inflammation Mediators and Chlamydia Pneumoniae," *Brit., J. Surgery*, 88(7):935-940, Feb. 2001.
Walton, L.J. et al., "Inhibition of Prostoglandin E2 Synthesis in Abdonminal Aortic Aneurysms," *Circulation*, 48-54, Jul. 6, 1999.
Xu, Q. et al., "Sp1 Increases Expression of Cyclooxygenase-2 in Hypoxic Vascular Endothelium," *J. Biological Chemistry*, 275(32):24583-24589, Aug. 2000.

\* cited by examiner

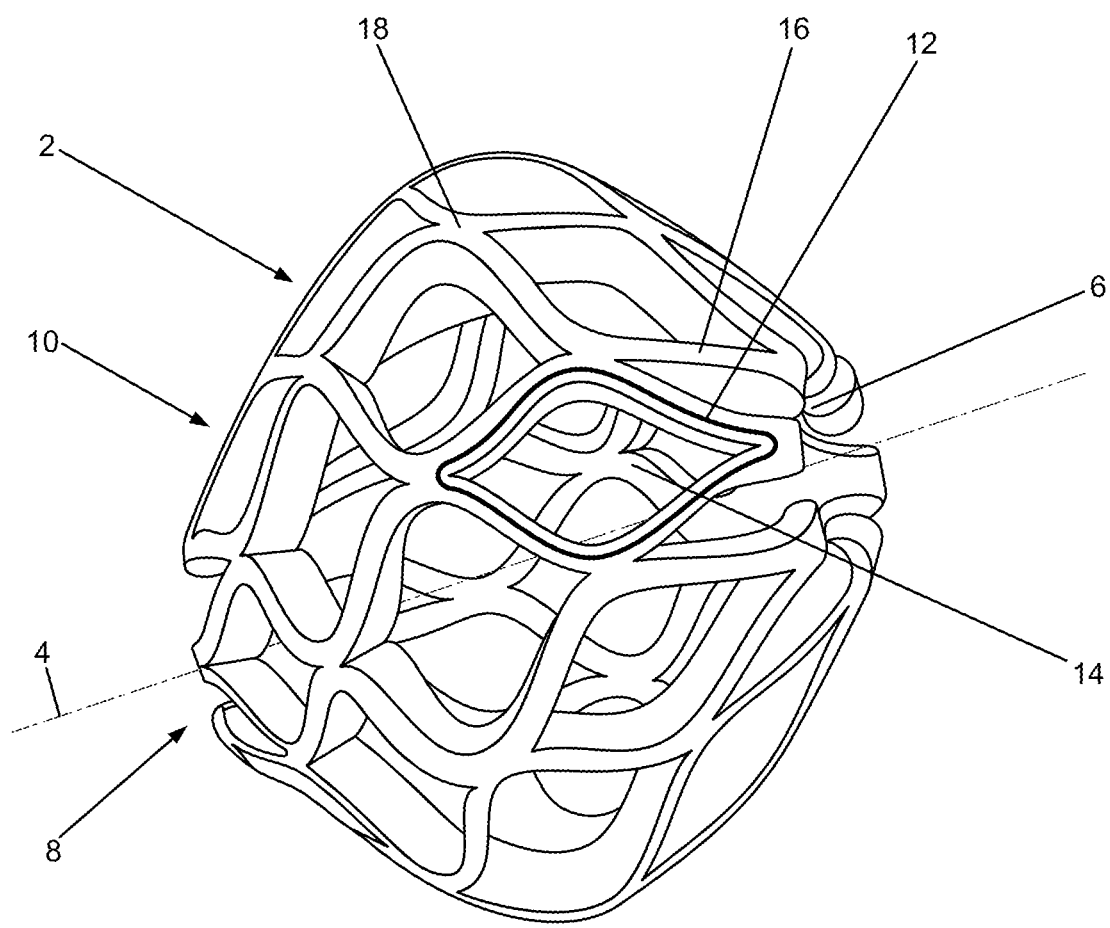
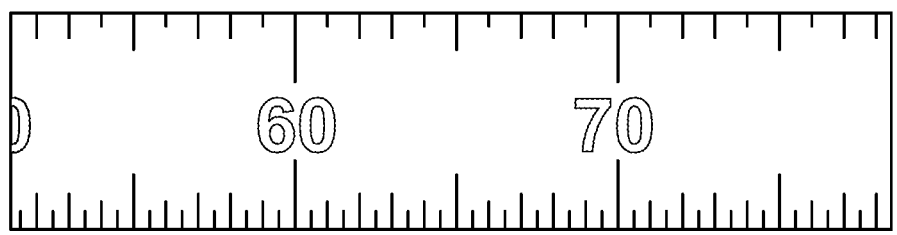
Fig. 1

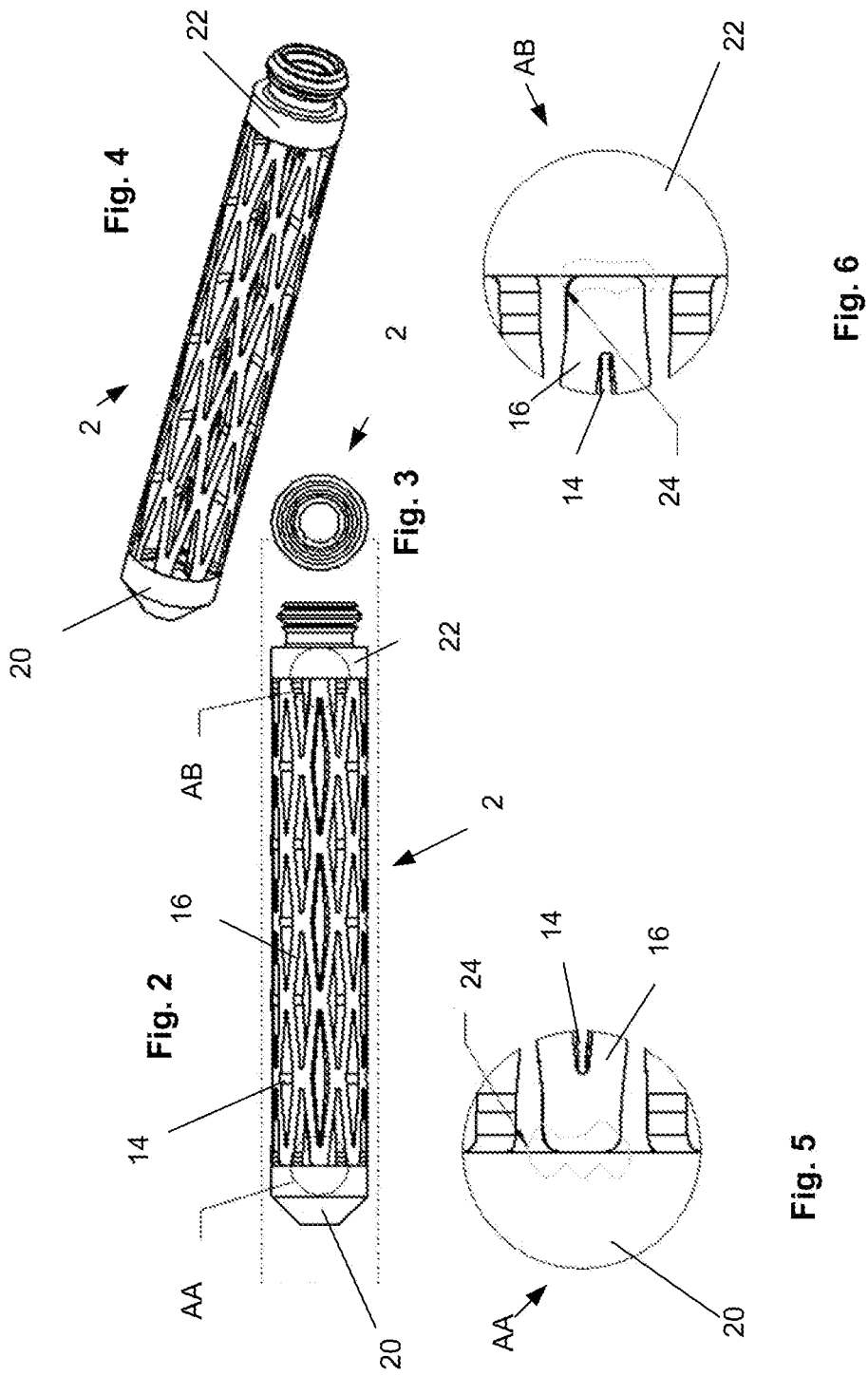

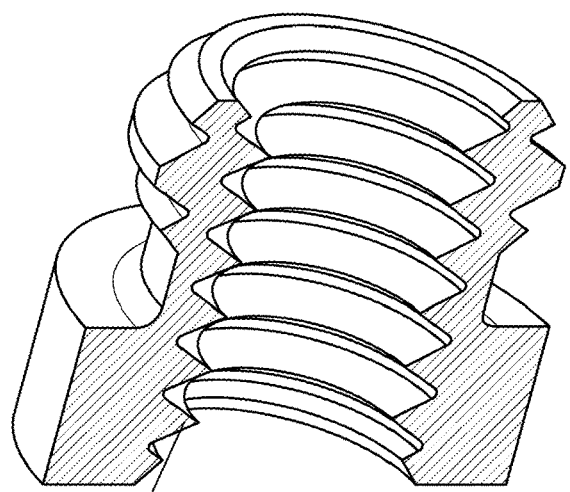
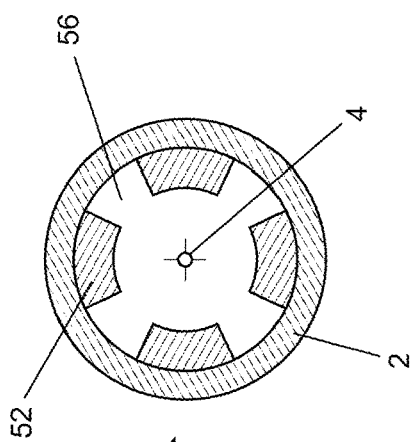
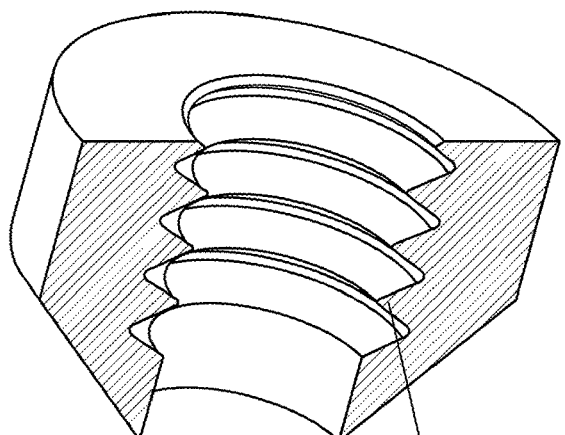

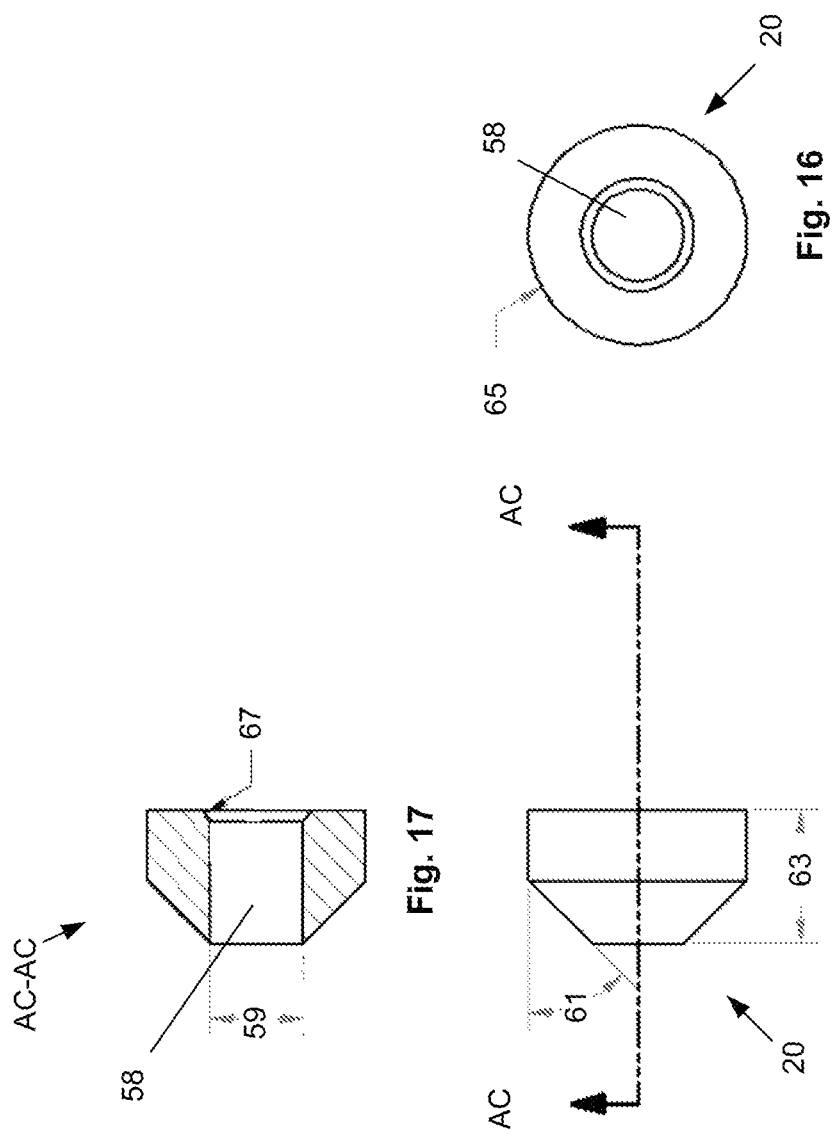

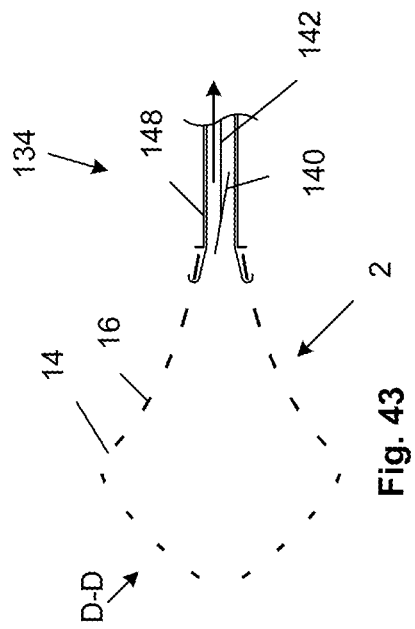
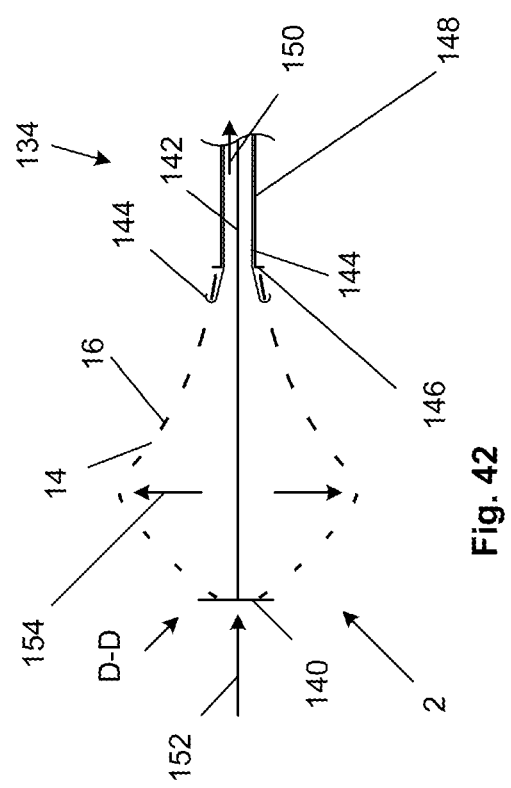

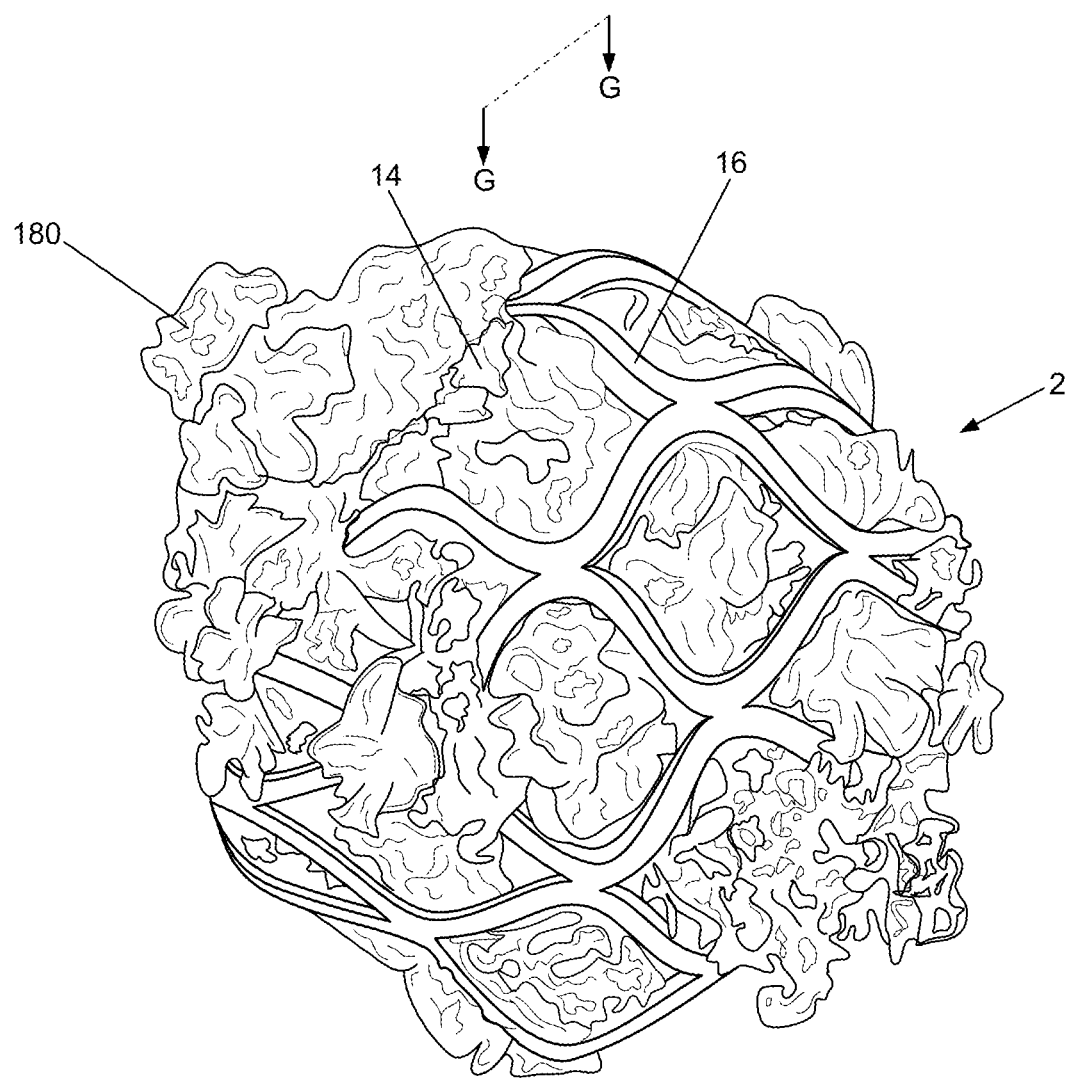
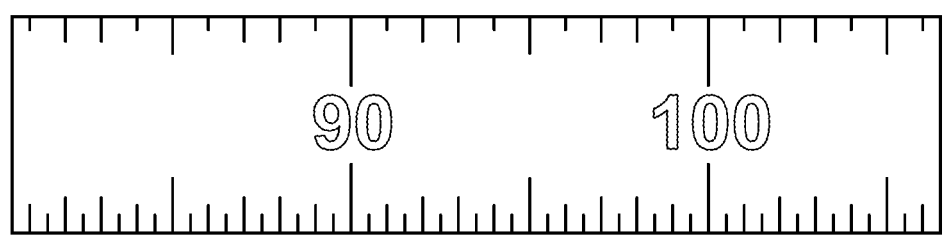
Fig. 56

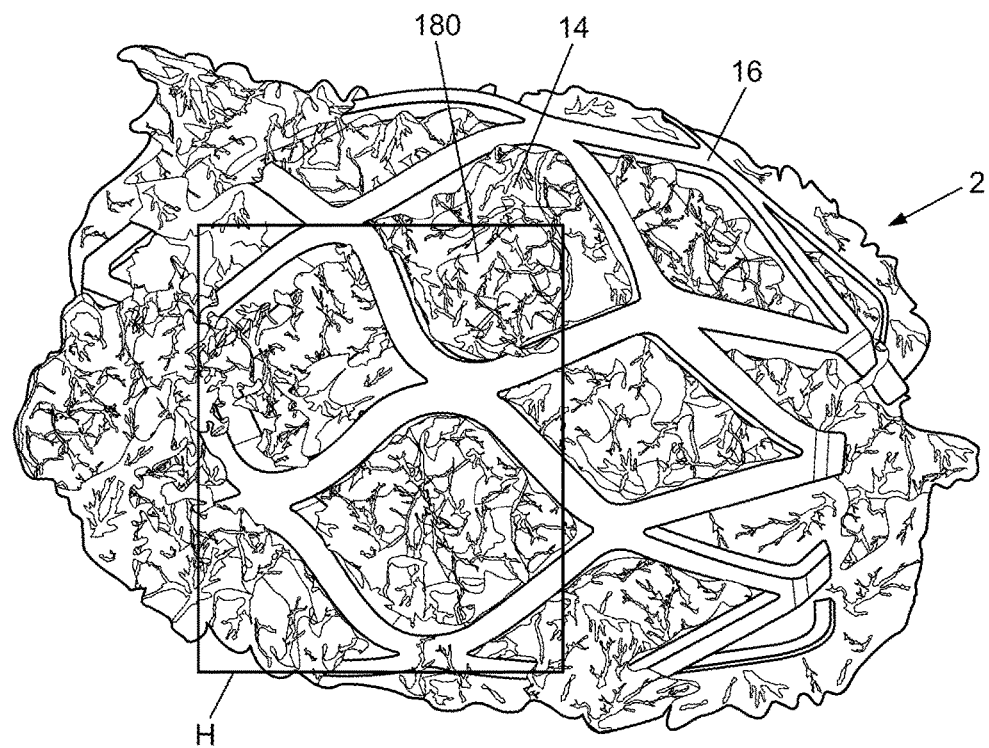
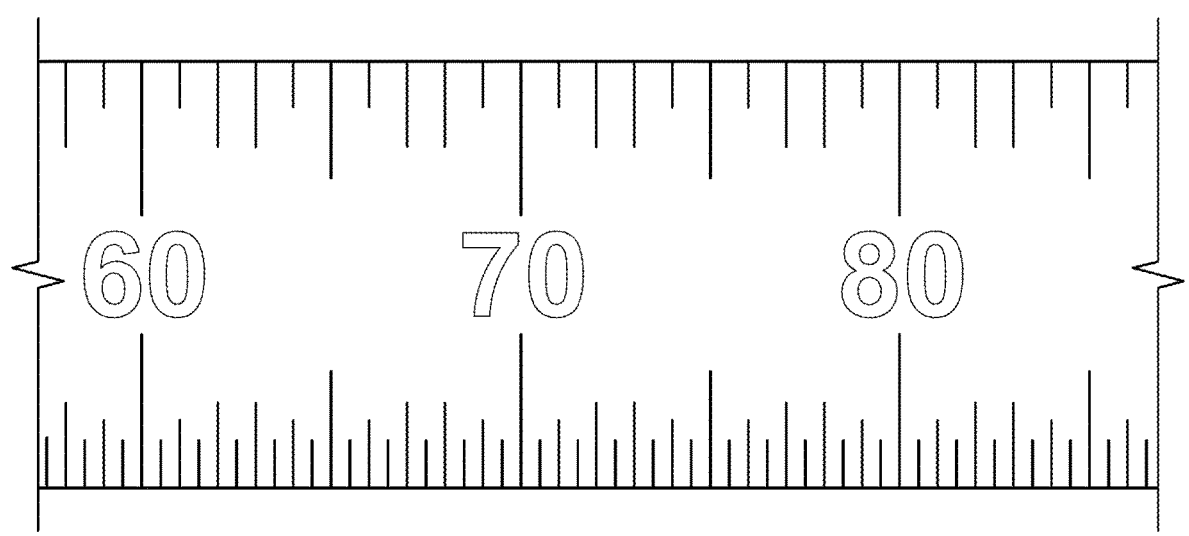
Fig. 57

EXPANDABLE SUPPORT DEVICE AND METHOD OF USE

CROSS-REFERENCE TO RELATED APPLICATIONS

This application is a continuation application of U.S. patent application Ser. No. 13/216,123, filed Aug. 23, 2011, which is a divisional application of U.S. patent application Ser. No. 12/260,971, filed Oct. 29, 2008, which is a continuation-in-part of PCT International Application No. PCT/US2007/067967, filed May 1, 2007, which claims the benefit of U.S. Provisional Application No. 60/796,915, filed May 1, 2006, which are herein incorporated by reference in their entireties.

BACKGROUND OF THE INVENTION

1. Field of the Invention

This invention relates to devices for providing support for biological tissue, for example to repair spinal compression fractures, and methods of using the same.

BRIEF SUMMARY OF THE INVENTION

An expandable support device for performing completely or partially implantable spinal repair is disclosed. The device has a first strut and a second strut attached to, and/or integral with, the first strut. The first strut is substantially deformable. The second strut can be substantially inflexible.

The device can be configured to expand in a radial direction during deployment in a bone. The device can be configured to contract in a longitudinal direction during deployment in a bone.

An expandable support device for repairing damaged bone is disclosed. The expandable support device can have a longitudinal axis. The expandable support device can have a first strut having a first strut cross-section. The expandable support device can have a second strut attached to, and/or integral with, the first strut. The first strut can be substantially deformable. The first strut cross-section can be configured to encourage bone growth toward the longitudinal axis.

The expandable support device can have a bone growth material. The first strut can have the bone growth material. The first strut can be coated with the bone growth material. The bone growth material can circumferentially surround the first strut cross-section.

The first strut can have a first strut first side closer to the longitudinal axis and a first strut second side farther from the longitudinal axis than the first strut first side, and the bone growth material can be on the first strut first side. The first strut second side can be substantially uncoated with the bone growth material.

The first strut cross-section can have a needle tip. The first strut cross-section can have a chisel tip. The first strut can have a thread extending radially therefrom. The first strut can have a longitudinal vane extending radially therefrom.

An apparatus for deploying and retrieving an expandable support device is a bone is disclosed. The apparatus can have a deployment rod. The deployment rod can have an expandable support device engager. The apparatus can have a retrieval sheath translatably slidable with respect to the deployment rod. The retrieval sheath can be configured to radially compress the expandable support device.

A method of retrieving a deployed expandable support device from a bone is disclosed. The method can include holding the expandable support device. The method can include translating a sheath over the expandable support device. Translating the sheath can include translating a rigid sheath. Holding can include holding a first end of the expandable support device. Translating can include radially compressing the expandable support device. The method can include translating the expandable support device out of the bone.

A method of deploying an expandable support device having a radius in a bone is disclosed. The method can include positioning the expandable support device in the bone. The method can also include radially expanding the expandable support device through the bone. The method can also include creating track voids. The method can also include deploying a material into the track voids, wherein the material encourages bone growth.

BRIEF DESCRIPTION OF THE DRAWINGS

FIG. 1 is a perspective view of a variation of the expandable support device in a radially expanded configuration.

FIG. 2 is a side view of a variation of the expandable support device in a radially compressed configuration.

FIG. 3 is a rear view of the variation of the expandable support device of FIG. 2 in a radially compressed configuration.

FIG. 4 is a perspective view of the variation of the expandable support device of FIG. 2 in a radially compressed configuration.

FIG. 5 is a close-up view of section AA of FIG. 2.

FIG. 6 is a close-up view of section AB of FIG. 2.

FIG. 14 illustrates cross-section C-C of the variation of the expandable support device in FIG. 13.

FIG. 15 is a side view of a variation of the distal attachment element.

FIG. 16 is a front view of a variation of the distal attachment element.

FIG. 17 illustrates a variation of cross-section AC-AC of FIG. 15.

FIG. 18 is a perspective view of a variation of cross-section AC-AC of FIG. 15.

FIG. 22 is a perspective view of a variation of cross-section AD-AD of FIG. 19.

FIGS. 42 and 43 illustrate cross-section D-D of a variation of a method for radially expanding the expandable support device of FIG. 40.

FIGS. 40, 41, and 44 through 47 illustrate the vertebra with a partial ventral sagittal cut-away for illustrative purposes.

FIGS. 56 and 57 illustrate variations of explants of the expandable support device with bone.

FIGS. 1, 40, 51, 45, 47, 56 and 57, are shown with exemplary length scales labeled in 10 mm increments and tabbed in ½ mm and 1 mm increments.

Figure 7:
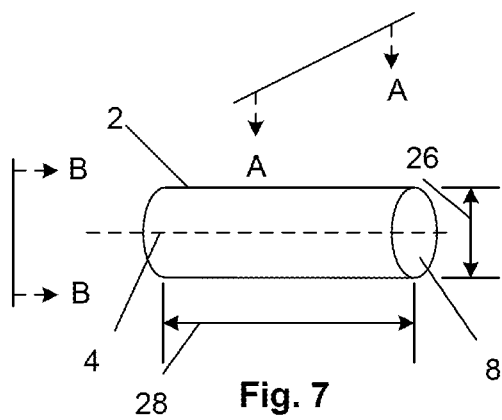
FIG. 7 illustrates a variation of the expandable support device in a radially contracted configuration.

Dimensions shown in FIGS. 15, 16, 17, 19 and 21 are merely examples. All dimensions can be from about 25% to about 400% of the dimensions shown in the figures, more narrowly from about 75% to about 125% of the dimensions shown in the figures.

DETAILED DESCRIPTION

FIG. 1 illustrates an expandable support device 2 in a radially expanded and longitudinally contracted configuration. The expandable support device 2 can be configured to be deployed in a treatment site, such as a bone, to provide mechanical support, for example to treat compression or other fractures or other structural bone failures. The expandable support device 2 can have a radially contracted and longitudinally expanded configuration, for example before deployment into a treatment site. The expandable support device 2 can have a radially expanded and longitudinally contracted configuration, for example after deployment into the treatment site.

The expandable support device 2 can have a longitudinal axis 4. The expandable support device 2 can have a distal port 6 at a longitudinally distal end and a proximal port 8 at a longitudinally proximal end. The expandable support device 2 can have a device radial side 10. The device side 10 can be substantially the surface defined by the cells 12 and pores 14, and for example, can exclude the proximal port 8 and the distal port 6.

The expandable support device 2 can have a number of struts 16 connected at joints 18. The struts 16 can be rigid and/or flexible. The struts 16 can be deformable and/or resilient. The joints 18 can be rigid and/or flexible. The joints 18 can be deformable and/or resilient.

The struts 16 and joints 18 can form enclosed shapes, such as cells 12. The cell 12 can dynamically act as a four-bar system (e.g., if the cell has four struts), five-bar system (e.g., if the cell has five struts), or another closed dynamic system correlating with the number of struts 16 and joints 18 of the cell.

The interior area of each cell can be a pore 14. The pores 14 can be open to the radial center of the expandable support device 2. The pores 14 can be substantially unobstructed. The pores 14 can encourage tissue (e.g., bone) growth toward the lumen or longitudinal channel of the expandable support device 2.

The device side can have a device side area 10. The radially (e.g., with respect to the longitudinal axis) external area joints 18 and struts 16 can be a solid surface area. The radially (e.g., with respect to the longitudinal axis) external area of the pores 14 can be a pore area. The ratio of the pore area to the device side area can be a pore ratio. With the expandable support device 2 in a radially expanded configuration, the pore ratio can be from about 20% to about 99%, more narrowly from about 50% to about 98%, yet more narrowly from about 75% to about 95%, for example about 80% or about 85% or about 90%.

Additional exemplary variations, features, elements and methods of use of the expandable support device and tools for deploying the expandable support device are described in PCT Patent Application Serial Numbers PCT/US05/034115 filed 21 Sep. 2005; PCT/US05/034742 filed 27 Sep. 2005; PCT/US05/034728 filed 27 Sep. 2005; PCT/US2005/037126 filed 12 Oct. 2005; and U.S. Provisional Patent Application Nos. 60/675,543 filed 27 Apr. 2005; 60/741,201 filed 1 Dec. 2005; 60/741,197 filed 1 Dec. 2005; 60/751,882 filed 19 Dec. 2005; 60/675,512 filed 27 Apr. 2005; 60/752,180 filed 19 Dec. 2005; 60/699,577 filed 14 Jul. 2005; 60/699,576 filed 14 Jul. 2005; 60/754,492 filed 28 Dec. 2005; 60/751,390 filed 15 Dec. 2005; 60/752,186 filed 19 Dec. 2005; 60/754,377 filed 27 Dec. 2005; 60/754,227 filed 28 Dec. 2005; 60/752,185 filed 19 Dec. 2005; and 60/752,182 filed 19 Dec. 2005; all of which are incorporated by reference herein in their entireties.

FIGS. 2, 3 and 4 illustrate that a distal end of the expandable support device 2 can be attached to and/or integral with a distal releasable attachment element 20. The proximal end of the expandable support device 2 can be attached to and/or integral with a proximal releasable attachment element 22.

FIG. 5 illustrates that the distal releasable attachment element 20 can be fixedly or removably attached to the expandable support device 2 at one or more attachment points 24. The attachment points 24 can be welds, press fits, adhesive, integrated elements, or combinations thereof.

FIG. 6 illustrates that the proximal releasable attachment element 22 can be fixedly or removably attached to the expandable support device 2 at one or more attachment points 24. The proximal releasable attachment element 22 can have a varying outer diameter along its length. The outer diameter of the proximal releasable attachment element 22 act as an interface, for example to be engaged by a deployment tool.

FIG. 7 illustrates that the expandable support device 2 can have a radially contracted configuration. The expandable support device 2 can have a contracted diameter 26 and an expanded length 28. The expandable support device 2 can have a substantially cylindrical shape.

Figure 8:
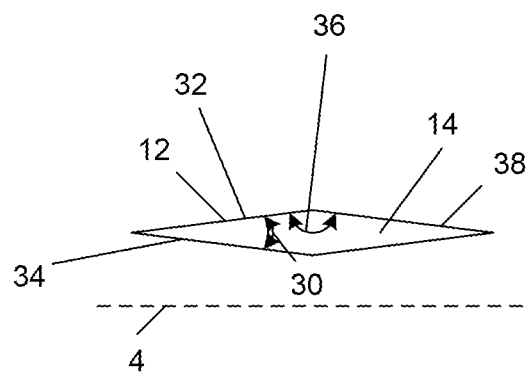
FIG. 8 illustrates a variation of a cell of the expandable support device of FIG. 7.

FIG. 8 illustrates that the cell 12 can have at least one longitudinal cell angle 30. The longitudinal cell angle 30 can be the angle formed between a first strut 32 and a second strut 34. The longitudinal cell angle 30 can face in a substantially parallel, or otherwise aligned, direction to the longitudinal axis 4.

The cell 12 can have at least one transverse cell angle 36. The transverse cell angle 36 can be the angle formed between the first strut 32 and a third strut 38. The transverse cell angle 36 can face in a substantially perpendicular or otherwise misaligned direction to the longitudinal axis 4. The transverse cell angle 36 can face in a substantially perpendicular or otherwise misaligned direction to the longitudinal cell angle 30.

Figure 9:
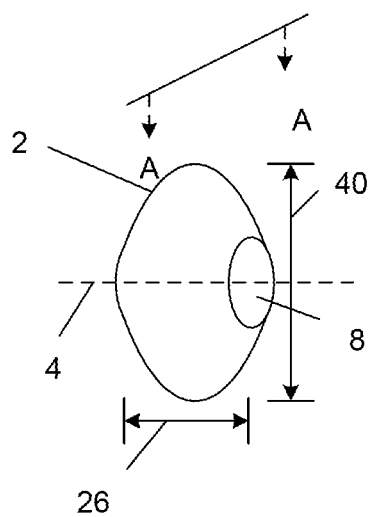
FIG. 9 illustrates a variation of the expandable support device in a radially expanded configuration.

FIG. 9 illustrates that the expandable support device 2 can have a radially expanded configuration. The expandable support device 2 can have an expanded diameter 40 and a contracted length 42. The expanded diameter 2 can be greater than the contracted diameter 26. The contracted length 42 can be less than the expanded length 28. The expandable support device 2 can have a substantially spherical, toroid or cubical shape.

Figure 10:
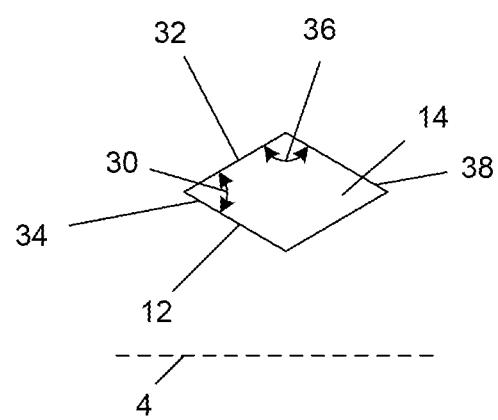
FIG. 10 illustrates a variation of a cell of the expandable support device of FIG. 9.

FIG. 10 illustrates that transverse cell angle 36 in the cell 12 from the expandable support device 2 having the radially expanded configuration can be smaller than the cell angle 36 in the cell from the expandable support device 2 having the radially contracted configuration. The longitudinal cell angle 30 in the cell 12 from the expandable support device 2 having the radially expanded configuration can be larger than the cell angle 36 in the cell 12 from the expandable support device 2 having the radially contracted configuration.

Figure 11:
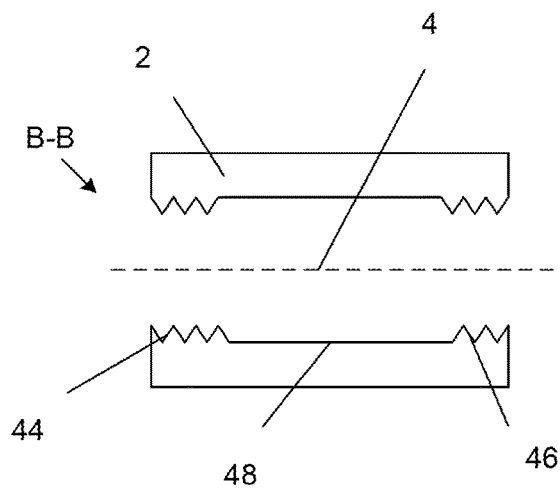
FIGS. 11-13 illustrate cross section B-B of various variations of the expandable support device.

FIG. 11 illustrates that the expandable support device 2 can have releasable attachment elements at the distal and/or proximal ends. For example, the expandable support device 2 can have distal device threads 44 and/or proximal device threads 46. The device mid-length section 48 can be bare of threads. The releasable attachment elements can be controllably removably attached to a deployment tool and/or the remainder of the expandable support device 2.

Figure 12:
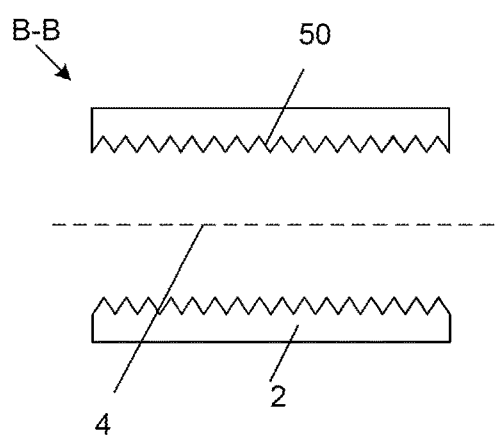

FIG. 12 illustrates that the device threads 50 can be continuous and/or substantially continuous from the proximal to the distal end (i.e., including the device mid-length section 48) of the expandable support device 2.

Figure 13:
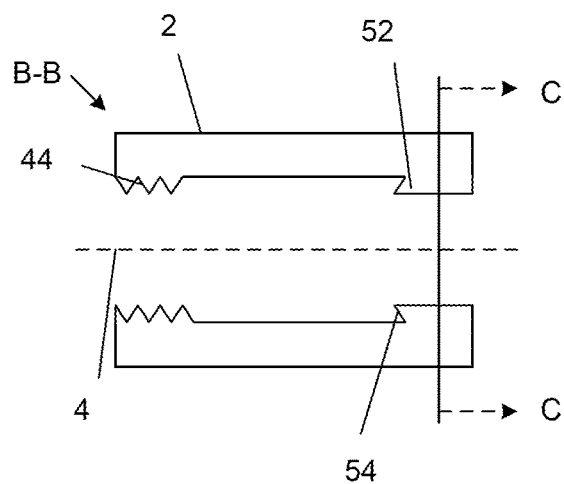
Figure 20:
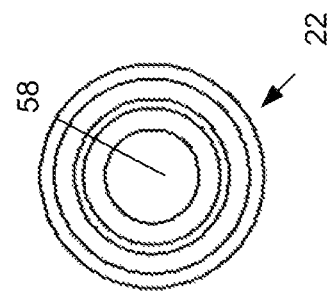
FIG. 20 is a rear view of a variation of the proximal attachment element.
Figure 21:
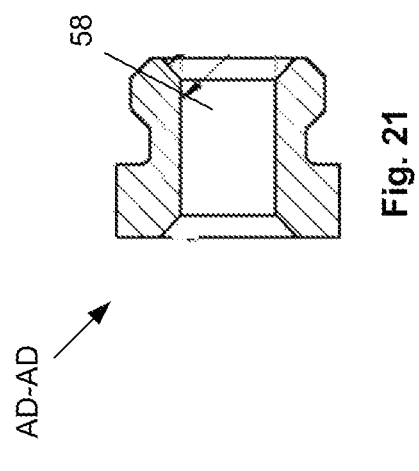
FIG. 21 illustrates a variation of cross-section AD-AD of FIG. 19.
Figure 19:
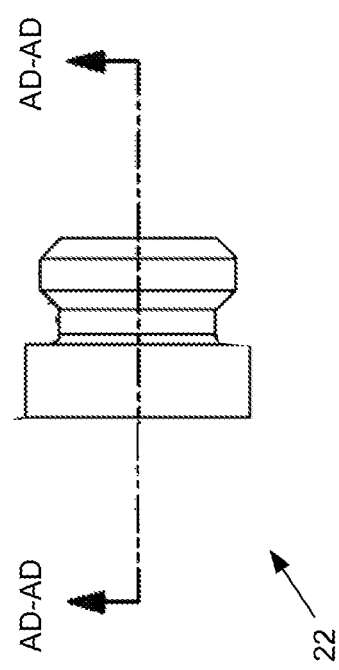
FIG. 19 is a side view of a variation of the proximal attachment element.

FIGS. 13 and 14 illustrates that the releasable attachment element, such as the proximal releasable attachment element 22, can be one or more device keys 52. The device keys 52 can have device key distal ends 54. The device key distal ends 54 can protrude in the distal direction and, for example can be sharpened. Device key ports 56 can be angularly between the device keys 52. The releasable attachment devices can be threads, keys, tabs, luers, or combinations thereof.

FIGS. 15, 16, 17 and 18 illustrate that the distal releasable attachment element 20 can have an internal channel 58. The internal channel 58 can have an internal channel diameter 59. The internal channel diameter 59 can be from about 1 mm (0.4 in.) to about 3 mm (0.1 in.), for example about 1.99 mm (0.0785 in.)

The distal releasable attachment element 20 can have distal device threads 44 (shown in FIG. 18).

The distal releasable attachment element 20 can have a sharpened distal end. The sharpened distal end can be used, for example, to push through bone during use. The sharpened distal end can have a sharpened distal end angle 61. The sharpened distal end angle 61 can be from about 20° to about 70°, for example about 45°.

The distal releasable attachment element 20 can have a distal releasable attachment element length 63. The distal releasable attachment element length 63 can be from about 13 mm (0.051 in.) to about 5 mm (0.2 in.), for example about 2.92 mm (0.115 in.).

The distal releasable attachment element 20 can have a distal releasable attachment element outer diameter 65. The distal releasable attachment outer diameter 65 can be from about 2.5 mm (0.098 in.) to about 10 mm (0.4 in.), for example about 4.78 mm (0.188 in.).

The distal releasable attachment element 20 can have an inner chamfer 67. The inner chamfer 67 can have an angle of about 45° from the adjacent sides and can have a length of about 0.2 mm (0.009 in.).

FIGS. 19, 20, 21 and 22 illustrate that the proximal releasable attachment element 22 can have the internal channel 58. The distal releasable attachment element 20 can have distal device threads 44 (shown in FIG. 18). The distal releasable attachment element 20 can have an engagable (e.g., lipped or notched) proximal end. The engagable proximal end can be configured, for example, to releasably engage a deployment tool.

Figure 23:
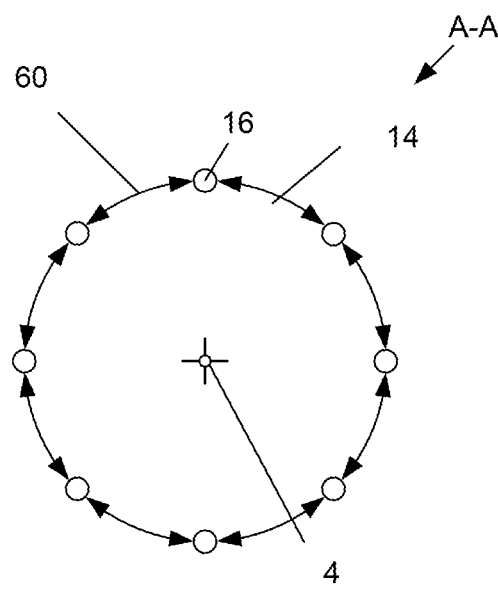
FIGS. 23 through 38 illustrate various variations of section A-A of FIG. 9.

FIG. 23 illustrates that the struts 16 can define a circular or oval cross-section of the expandable support device 2 in a given cross-section A-A. The pores 14 can have pore angles 60 with respect to the longitudinal axis 4 in cross-section, as shown. The pore angles 60 can vary around the cross-section of the expandable support device 2 (i.e., as the pores get closer to distal and proximal joints, the pore angles approach zero). The struts 16 can have uniform (as shown) or various cross-sectional configurations. The struts 16 can have substantially circular cross-sections, as shown in FIG. 10.

Figure 24:
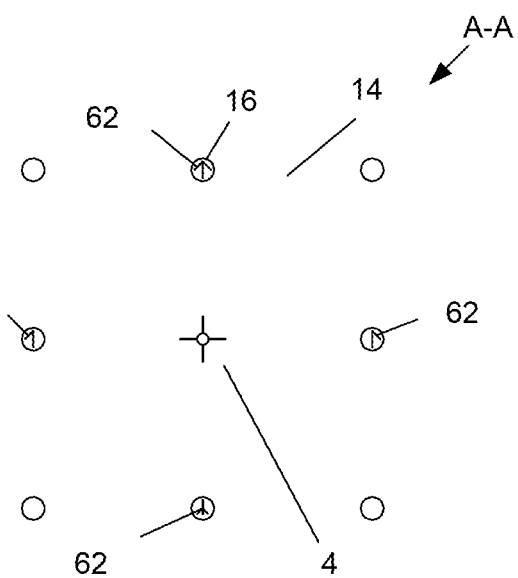

FIG. 24 illustrates that the struts 16 can form a square or rectangular cross-section of the expandable support device 2 in a given cross-section A-A. One or more of the struts 16 can have markers 62, such as radiopaque and/or echogenic markers. The markers 62 can be unique for each strut 16. For example, the markers 62 can identify the deployment orientation, as shown (e.g., arrows pointing in the up direction for deployment, with the top strut's marker showing a top arrow; the left strut's marker showing an arrow with only a left arrow-end; the right strut's marker showing an arrow with only a left arrow-end; and the bottom strut's marker showing an arrow with the arrowhead near the bottom of the arrow).

Figure 25:
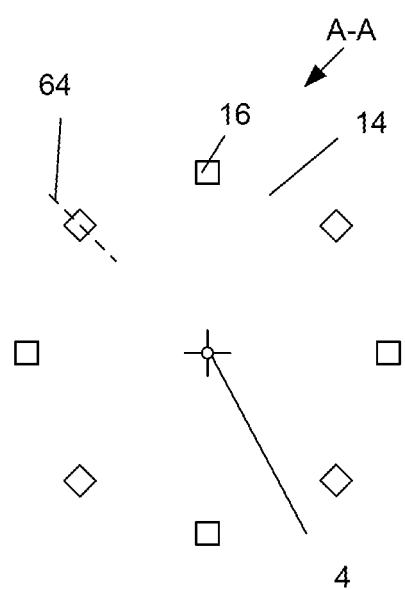

FIG. 25 illustrates that the struts 16 can have substantially square or rectangular cross-sectional configurations. The struts 16 and joints 14 (not shown, and understood to be substantially represented when describing the struts in cross-sections A-A) can have first rectilinear axes 64. The first rectilinear axes 64 can substantially or completely intersect the longitudinal axis 4 in a given cross-section A-A. Expandable support devices 2 that do not have circular or ovular transverse cross-sections (i.e., the shapes defined by the struts and pores shown in cross-section A-A), such as square, rectangular, triangular transverse cross-sections, or combinations thereof, can have one or more struts 16 with rectilinear axes 64 that do not substantially intersect the longitudinal axis 4 in a given cross-section A-A.

Figure 26:
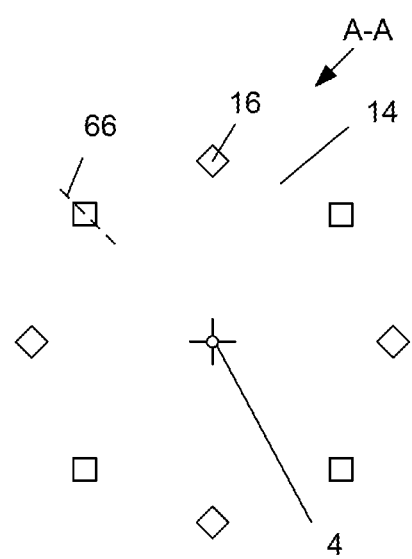

FIG. 26 illustrates that the struts 16 and joints 14 (not shown) can have diametric or diagonal axes 66 in a given cross-section A-A. The diametric or diagonal axes 66 can substantially or completely intersect the longitudinal axis 4. Expandable support devices 2 that do not have circular or ovular transverse cross-sections (i.e., the shapes defined by the struts and pores shown in cross-section A-A), such as square, rectangular, triangular transverse cross-sections, or combinations thereof, can have one or more struts 16 with diametric or diagonal axes 66 that do not substantially intersect the longitudinal axis 4 in a given cross-section A-A. The struts 16 can have square or rectangular cross-sectional configurations.

Figures 27, 28:
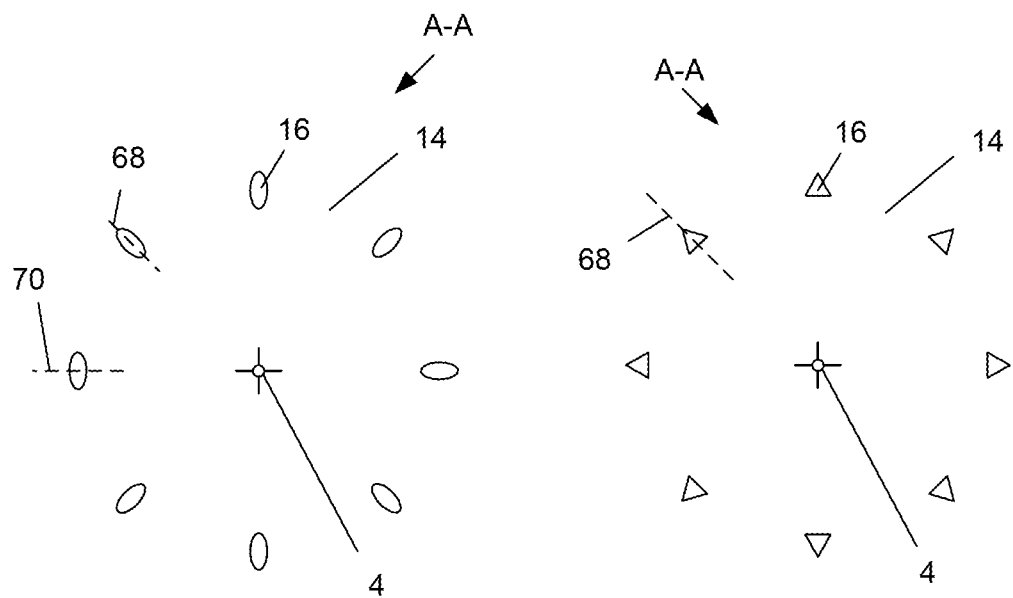

FIG. 27 illustrates that the struts 16 and joints 14 (not shown) can have rectangular or oval (as shown) cross-sectional configurations or other cross-sectional configurations with primary and secondary axes. The oval cross-sections can each have a major (i.e., primary) axis 68. The oval cross-sections can each have a minor (i.e., secondary) axis 70 in a given cross-section A-A. The major axes 68 can substantially or completely intersect the longitudinal axis 4. The minor axes 70 can substantially or completely intersect the longitudinal axis 4. Expandable support devices 2 that do not have circular or ovular transverse cross-sections (i.e., the shapes defined by the struts and pores shown in cross-section A-A), such as square, rectangular, triangular transverse cross-sections, or combinations thereof, can have one or more struts 16 with major 68 and/or minor axes 70 that do not substantially traverse the longitudinal axis 4 in a given cross-section A-A.

FIG. 28 illustrates that the struts 16 and joints 14 (not shown) can have triangular (e.g., diagonal, right, isosceles, equilateral) cross-sectional configurations. The triangular configurations can each have the major axis 68.

Figures 29, 30:
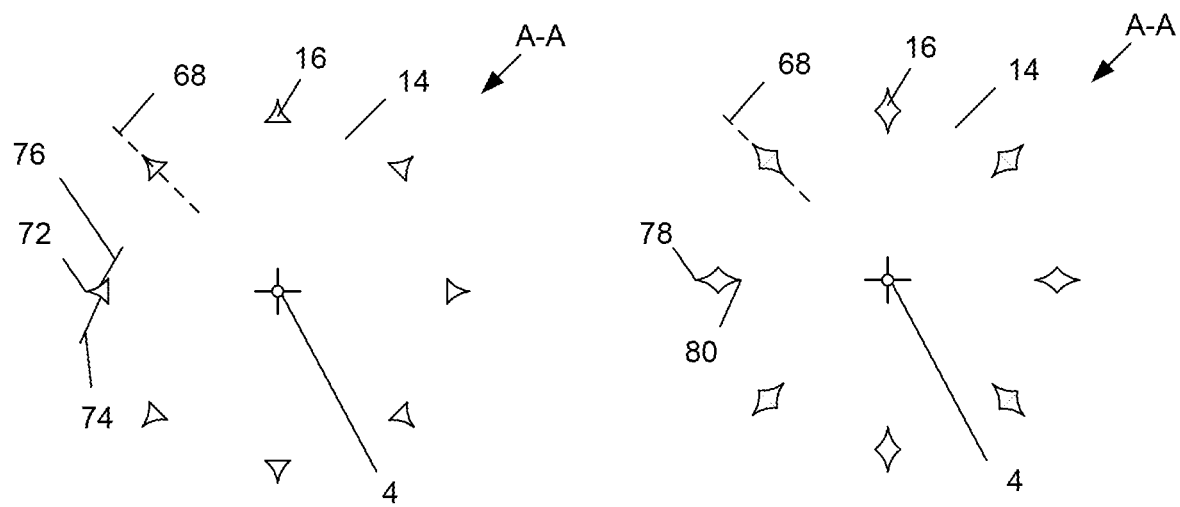

FIG. 29 illustrates that the struts 16 and joints 14 (not shown) can have needle tips 72, for example with a triangular configuration cross-sectional configuration. The needle tip 72 can have a first needle side 74 and a second needle side 76. One or both needle sides can be concave inward. The needle tip 72 can have a needle tip angle from about 0.1° to about 30°, more narrowly from about 0.5° to about 25°, yet more narrowly from about 2° to about 20°, for example about 5° or about 10° or about 15°.

FIG. 30 illustrates that the struts 16 and joints 14 (not shown) can each have a first needle tip 78 pointed radially outward, and a second needle tip 80 pointed radially inward. The major axis 68 can be the major axis for the first and second needle tips 78, 80.

Figure 31:
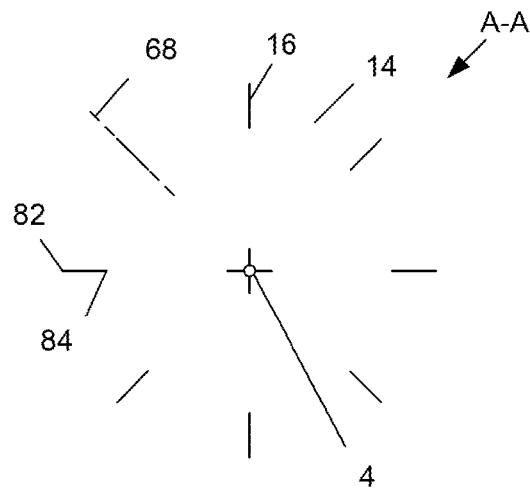

FIG. 31 illustrates that the struts 16 and joints 14 (not shown) can have a first tip 82 and a second tip 84 along the major axis 68. The struts 16 can be of nominal or otherwise substantially no thickness in directions other than the major axis 68.

Figure 32:
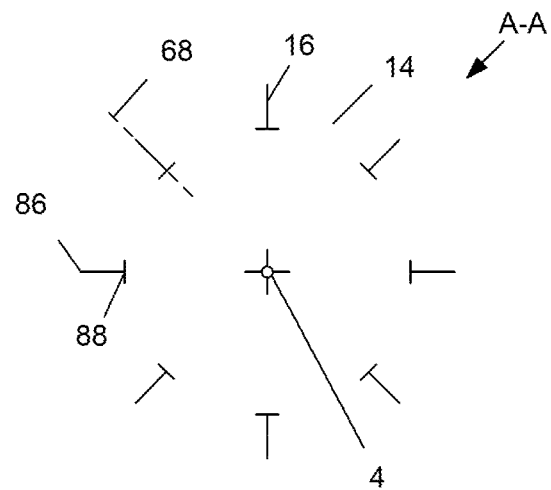

FIG. 32 illustrates that the struts 16 and joints 14 (not shown) can have a nail-like configuration. The struts 16 can have a tip 86 running on the major axis 68. The struts 16 can have a head 88, for example, at about a 90° angle to the tip 86 and/or to the major axis 68.

Figure 33:
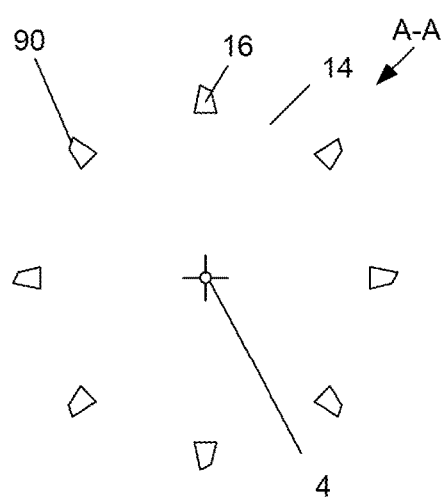

FIG. 33 illustrates that the struts 16 and joints 14 (not shown) can have chisel tips 90. The struts 16 can have quadrilateral (e.g., bicentric quadrilateral, cyclic quadrilateral, orthocentric quadrilateral, rational quadrilateral), parallelogram (e.g., medial parallelogram), rhombus (e.g., golden rhombus), kite, lozenge, trapezoid (e.g., isosceles trapezoid), tetrahedron cross-sectional configuration or combinations thereof.

Figure 34:
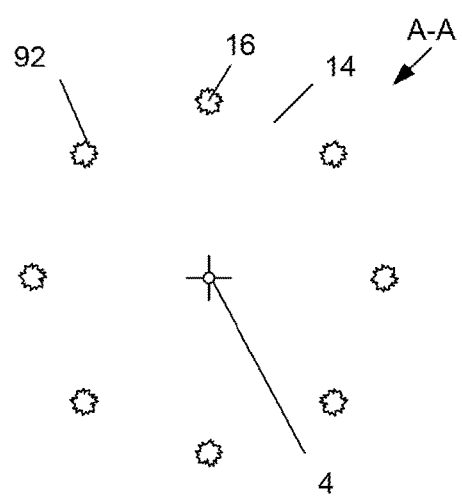

FIG. 34 illustrates that the struts 16 and joints 14 (not shown) can have randomly-shaped surface 92 configurations. The randomly-shaped surface 92 configurations can have an irregular surface defined by a random or quasi-random configuration.

Figure 35:
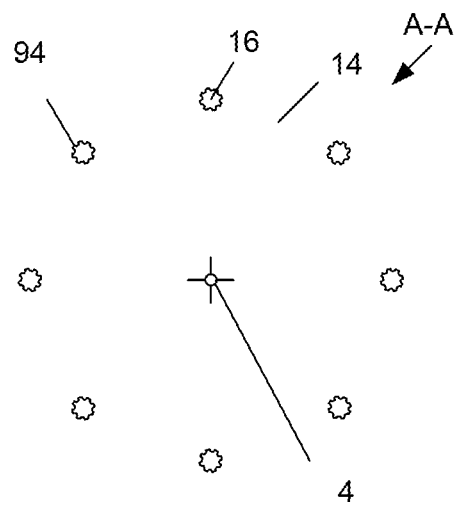

FIG. 35 illustrates that the struts 16 can have a textured (e.g., non-randomly surfaced) surface 94 configuration. For example, the textured surface 94 configuration can have a knurled, convex or concave dimpled or bumped, transversely and/or longitudinally and/or diagonally checkered or grooved (as shown), or brushed configuration, or combinations thereof.

Figure 36:
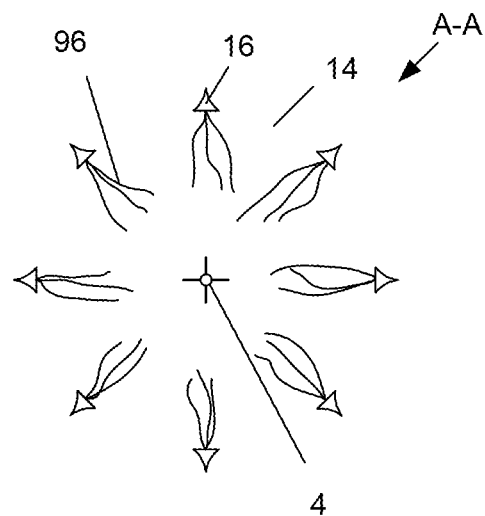

FIG. 36 illustrates that the struts 16 can each have one or more threads and/or longitudinal vanes 96 attached to or integral therewith. The threads and/or vanes 96 can extend radially toward the longitudinal axis 4. The threads and/or vanes 96 can have a coating or be made partially or completely from any material listed herein, such as cements and/or fillers and/or glues (e.g., bone morphogenic protein, morselized bone, additional examples listed infra), such as for soliciting or otherwise encouraging bone growth. The threads and/or vanes 96 can be flexible or rigid. The threads and/or vanes 96 can be resilient and/or deformable. The threads and/or vanes 96 can be made in whole or part from a bioresorbable, bioabsorbable or biodegradable material. The various threads and/or vanes 96 can have uniform or variable lengths.

Figure 37:
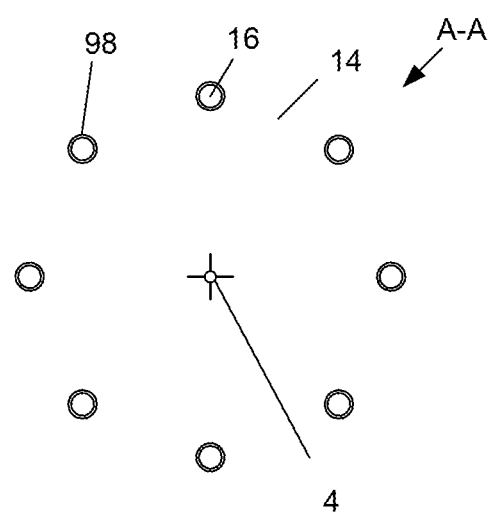
Figure 38:
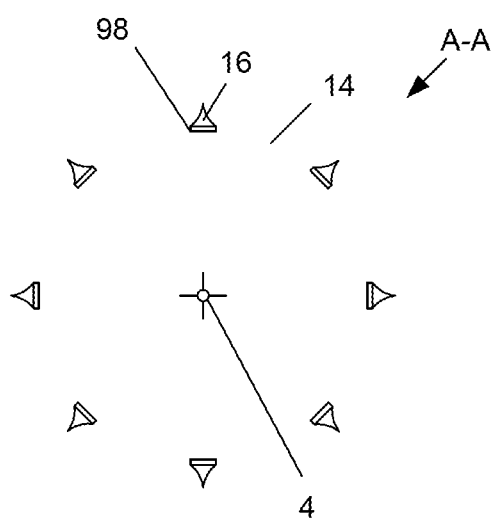

FIG. 37 illustrates that the struts 16 can be wholly (as shown) or partially coated and/or otherwise covered by a coating and/or matrix 98 of any material listed herein. FIG. 38 illustrates that the struts 16 can be coated and/or be otherwise covered by a material listed herein on the side of the strut 16 facing the longitudinal axis 4. The side of the strut 16 not facing the longitudinal axis 4 can have no coating neither/nor be otherwise covered by a material other than the material of the original non-coated/covered strut.

Any or all elements of the expandable support device 2 and/or deployment tool and/or other devices or apparatuses described herein can be made from, for example, a single or multiple stainless steel alloys, nickel titanium alloys (e.g., Nitinol), cobalt-chrome alloys (e.g., ELGILOY® from Elgin Specialty Metals, Elgin, Ill.; CONICHROME® from Carpenter Metals Corp., Wyomissing, Pa.), nickel-cobalt alloys (e.g., MP35N® from Magellan Industrial Trading Company, Inc., Westport, Conn.), molybdenum alloys (e.g., molybdenum TZM alloy, for example as disclosed in International Pub. No. WO 03/082363 A2, published 9 Oct. 2003, which is herein incorporated by reference in its entirety), tungsten-rhenium alloys, for example, as disclosed in International Pub. No. WO 03/082363, polymers such as polyethylene teraphathalate (PET), polyester (e.g., DACRON® from E. I. Du Pont de Nemours and Company, Wilmington, Del.), polypropylene, aromatic polyesters, such as liquid crystal polymers (e.g., Vectran, from Kuraray Co., Ltd., Tokyo, Japan), ultra high molecular weight polyethylene (i.e., extended chain, high-modulus or high-performance polyethylene) fiber and/or yarn (e.g., SPECTRA® Fiber and SPECTRA® Guard, from Honeywell International, Inc., Morris Township, N.J., or DYNEEMA® from Royal DSM N.V., Heerlen, the Netherlands), polytetrafluoroethylene (PTFE), expanded PTFE (ePTFE), polyether ketone (PEK), polyether ether ketone (PEEK), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), poly-L-glycolic acid (PLGA), polylactic acid (PLA), poly-L-lactic acid (PLLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft, bone cement, morselized bone, osteogenic powder, beads of bone) any of the other materials listed herein or combinations thereof. Examples of radiopaque materials are barium sulfate, zinc oxide, titanium, stainless steel, nickel-titanium alloys, tantalum and gold.

Any or all elements of the expandable support device 2 and/or deployment tool and/or other devices or apparatuses described herein, can be, have, and/or be completely or partially coated with agents and/or a matrix a matrix for cell ingrowth or used with a fabric, for example a covering (not shown) that acts as a matrix for cell ingrowth. The matrix and/or fabric can be, for example, polyester (e.g., DACRON® from E. I. Du Pont de Nemours and Company, Wilmington, Del.), polypropylene, PTFE, ePTFE, nylon, extruded collagen, silicone or combinations thereof.

The expandable support device 2 and/or deployment tool and/or elements of the expandable support device 2 and/or elements of the deployment tool and/or other devices or apparatuses described herein and/or the fabric can be filled, coated, layered and/or otherwise made with and/or from cements, fillers, glues, and/or an agent delivery matrix known to one having ordinary skill in the art and/or a therapeutic and/or diagnostic agent. Any of these cements and/or fillers and/or glues can be osteogenic and osteoinductive growth factors.

Examples of such cements and/or fillers includes bone chips, demineralized bone matrix (DBM), calcium sulfate, corallin hydroxyapatite, biocoral, tricalcium phosphate, calcium phosphate, polymethyl methacrylate (PMMA), biodegradable ceramics, bioactive glasses, hyaluronic acid, lactoferrin, bone morphogenic proteins (BMPs) such as recombinant human bone morphogenetic proteins (rhBMPs), other materials described herein, or combinations thereof.

The agents within these matrices can include any agent disclosed herein or combinations thereof, including radioactive materials; radiopaque materials; cytogenic agents; cytotoxic agents; cytostatic agents; thrombogenic agents, for example polyurethane, cellulose acetate polymer mixed with bismuth trioxide, and ethylene vinyl alcohol; lubricious, hydrophilic materials; phosphor cholerae; anti-inflammatory agents, for example non-steroidal anti-inflammatories (NSAIDs) such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, Pa.; indomethacin; mefenamic acid), COX-2 inhibitors (e.g., VIOXX® from Merck & Co., Inc., Whitehouse Station, N.J.; CELEBREX® from Pharmacia Corp., Peapack, N.J.; COX-1 inhibitors); immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Examples of other agents are provided in Walton et al, Inhibition of Prostoglandin E2 Synthesis in Abdominal Aortic Aneurysms, *Circulation*, Jul. 6, 1999, 48-54; Tambiah et al, Provocation of Experimental Aortic Inflammation Mediators and Chlamydia Pneumoniae, *Brit. J. Surgery* 88 (7), 935-940; Franklin et al, Uptake of Tetracycline by Aortic Aneurysm Wall and Its Effect on Inflammation and Proteolysis, *Brit. J Surgery* 86 (6), 771-775; Xu et al, Sp1 Increases Expression of Cyclooxygenase-2 in Hypoxic Vascular Endothelium, *J. Biological Chemistry* 275 (32) 24583-24589; and Pyo et al, Targeted Gene Disruption of Matrix Metalloproteinase-9 (Gelatinase B) Suppresses Development of Experimental Abdominal Aortic Aneurysms, *J. Clinical Investigation* 105 (11), 1641-1649 which are all incorporated by reference in their entireties.

Method of Use

Figure 39:
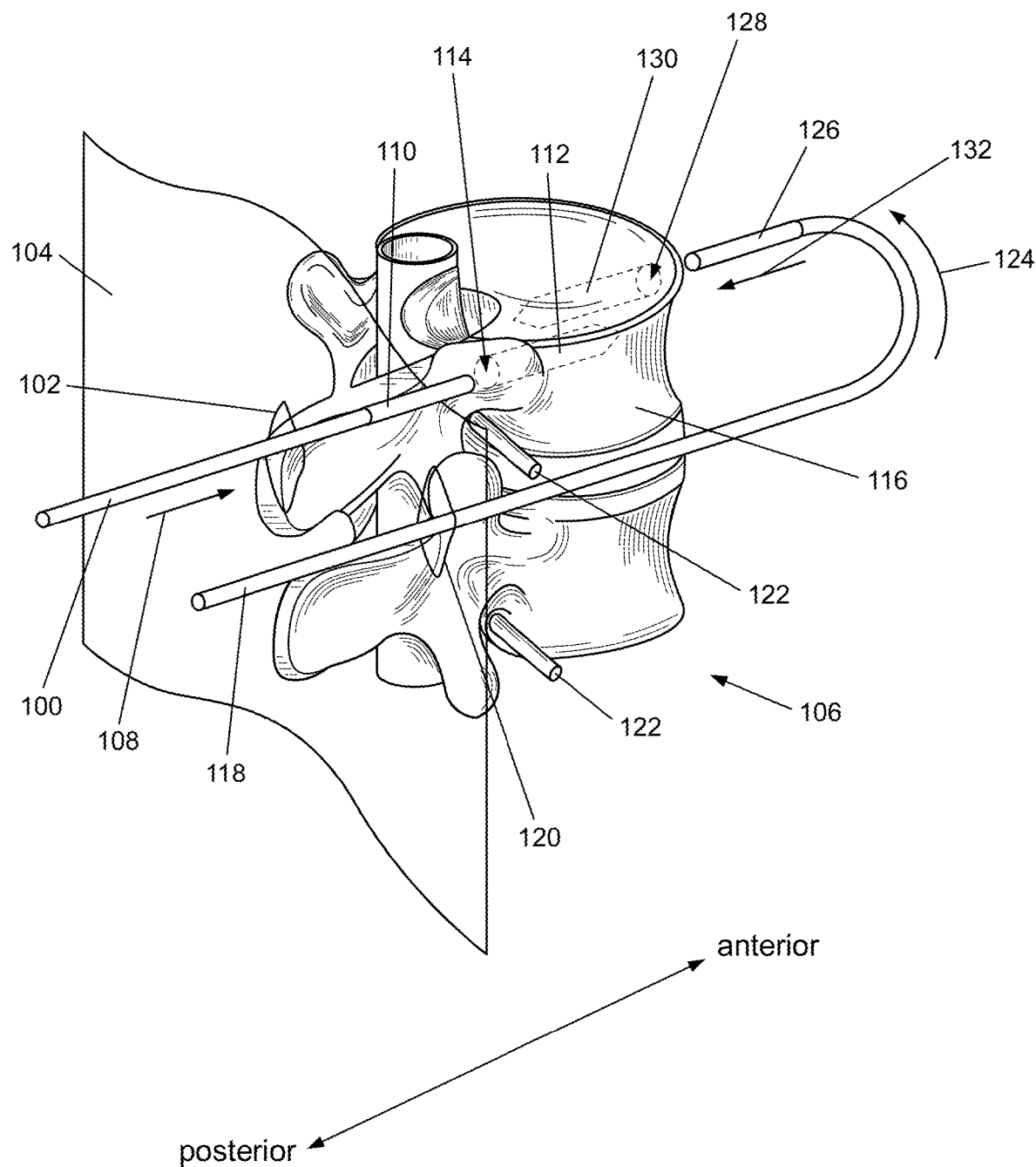
FIG. 39 illustrates various methods for deploying the expandable support device.

FIG. 39 illustrates that a first deployment tool 100 can enter through the subject's back. The first deployment tool 100 can enter through a first incision 102 in skin 104 on the posterior side of the subject near the vertebral column 106. The first deployment tool 100 can be translated, as shown by arrow 108, to position a first expandable support device 110 into a first damage site 112. The first access port 114 can be on the posterior side of the vertebra 116.

A second deployment tool 118 can enter through a second incision 120 (as shown) in the skin 104 on the posterior or the first incision 102. The second deployment tool 118 can be translated through muscle (not shown), around nerves 122, and anterior of the vertebral column 106. The second deployment tool 118 can be steerable. The second deployment tool 118 can be steered, as shown by arrow 124, to align the distal tip of the second expandable support device 126 with a second access port 128 on a second damage site 130. The second access port 128 can face anteriorly. The second deployment tool 118 can translate, as shown by arrow 132, to position the second expandable support device 126 in the second damage site 130.

The vertebra 116 can have multiple damage sites 112, 130 and expandable support devices 2 deployed therein. The expandable support devices 2 can be deployed from the anterior, posterior, both lateral, superior, inferior, any angle, or combinations of the directions thereof.

As shown in applications incorporated by reference herein, the expandable support device 2 can be inserted in the vertebra 116 in a radially contracted configuration. The expandable support device 2 can then be radially expanded.

Figure 40:
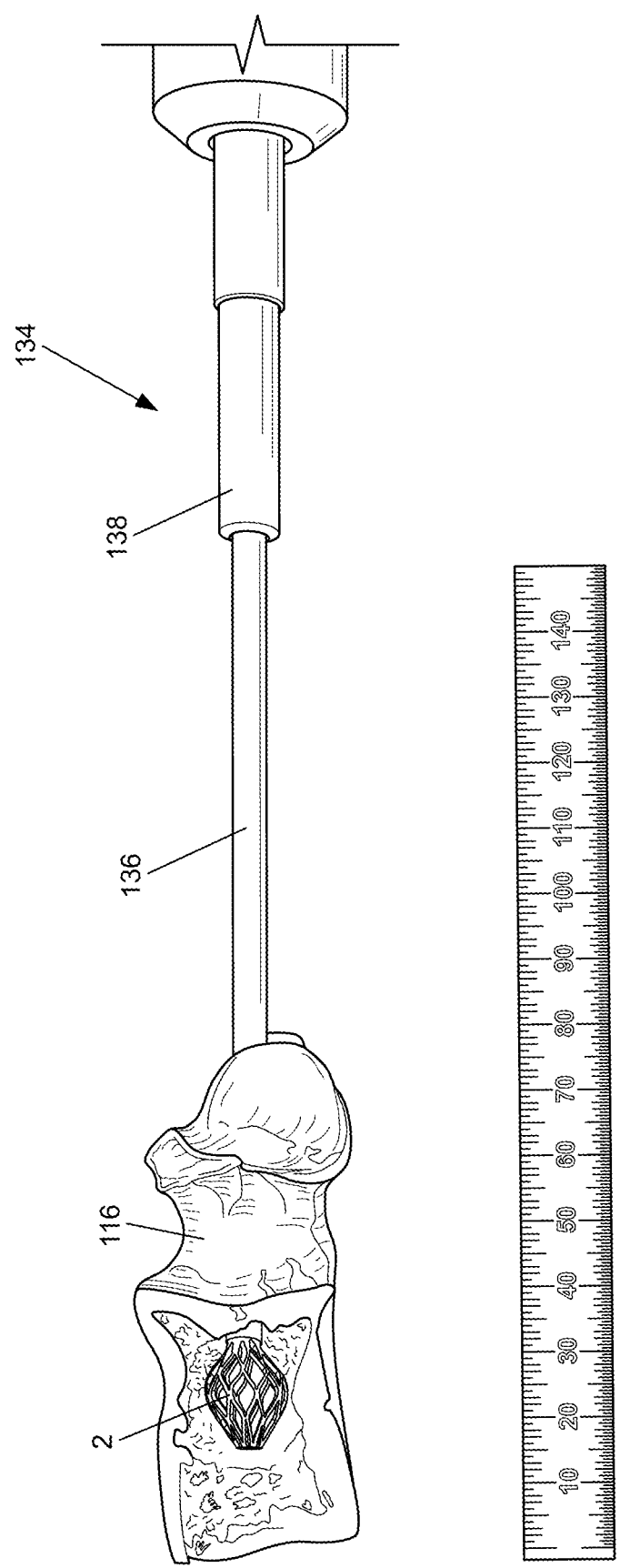
FIG. 40 illustrates a variation of a method of deploying the expandable support device with a deployment tool.

FIG. 40 illustrates the expandable support device 2 in a partially deployed, radially expanded configuration in the vertebra 116. The expandable support device 2 can be removably attached to the deployment tool 134. The deployment tool 134 can have a deployment rod sheath 136, as shown. The expandable support device 2 can be attached to a deployment rod and/or the deployment rod sheath 136.

Figure 41:
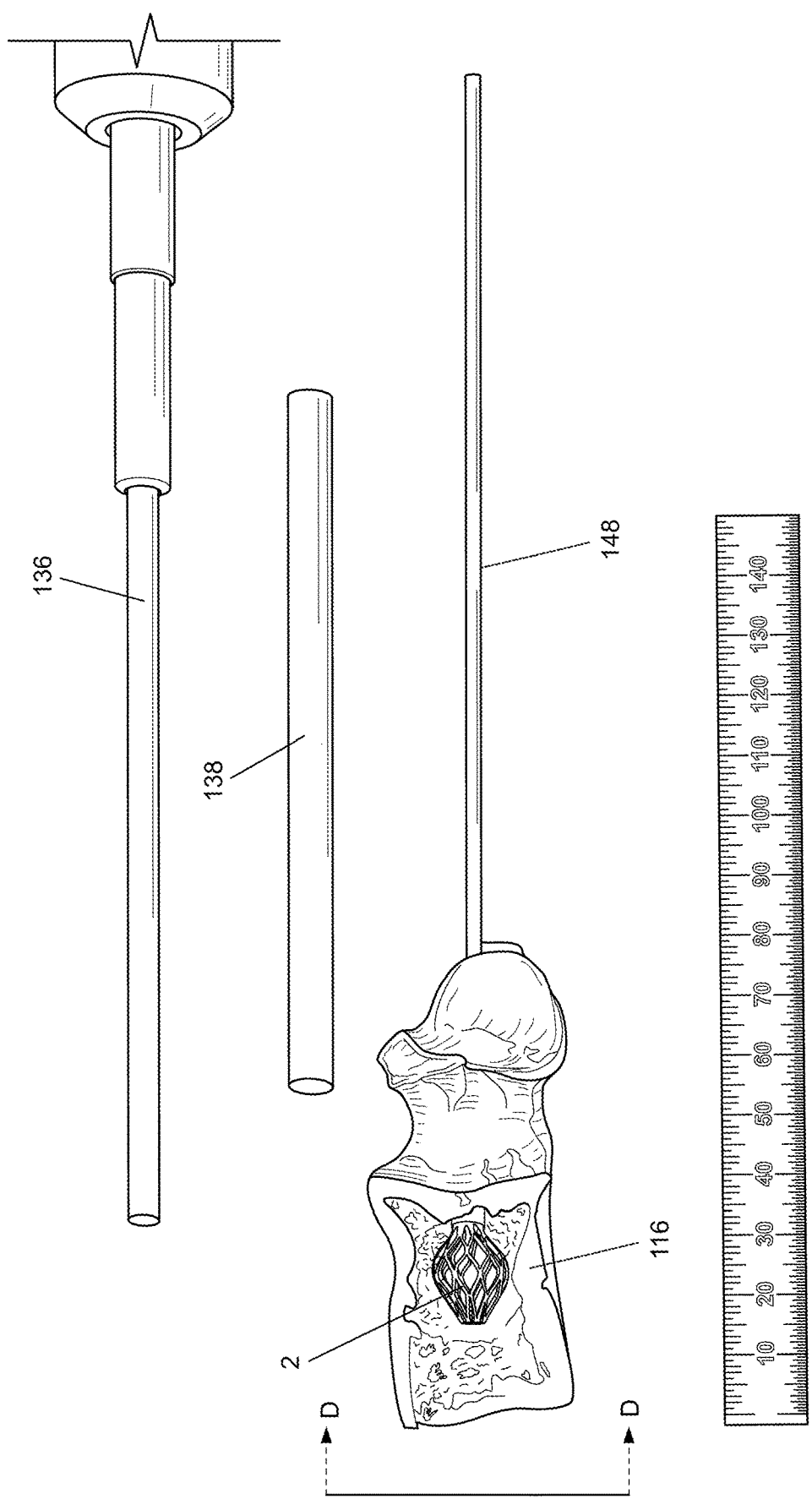
FIG. 41 illustrates the variation of FIG. 40 with the deployment tool in a partially disassembled configuration.

FIG. 41 illustrates FIG. 40 with the deployment tool 134 partially disassembled for illustrative purposes. The deployment tool 134 can have a recovery sheath 138. The recovery sheath 138 can be slidably attached over the deployment rod and/or the deployment rod sheath 136. The recovery sheath 138 can be hollow cylinder. The recovery sheath 138 can be translatably controlled by the deployment tool 134. The deployment rod sheath 136 can be slidably or fixedly attached to the deployment rod and/or the remainder of the deployment tool 134.

FIG. 42 illustrates that a deployment tool 134 can have a distal tool head 140 at the distal end of a distal tool shaft 142. The distal tool shaft 142 can be removably attached to the distal end of the expandable support device 2 (e.g., interference fit and/or threadably attached). The deployment tool 134 can have an engagement element 144 that can be removably attached (e.g., threadably attached and/or interference fit) to the proximal end of the expandable support device 2. For example, one or more struts 16 at the proximal end of the expandable support device 2 can be releasably compressed between the engagement element 144 and a proximal anvil 146 that can be attached to or integral with the deployment rod 148.

The distal tool shaft 142 can be translated proximally, as shown by arrow 150. The distal tool head 140 and the proximal anvil 146 can longitudinally compress, as shown by arrow 152, the expandable support device 2. The expandable support device 2 can then radially expand, as shown by arrow 154.

FIG. 43 illustrates that the distal tool head 140 can be removably attached (e.g., unscrewable, or unlockable—as a key, or retractable (e.g., rotatably, or otherwise compressably or condensably)) attached to the distal tool shaft 142. The distal tool head 140 can be retracted and the distal tool shaft 142 can be translated out of the expandable support device, as shown by arrow 150.

Figure 44:
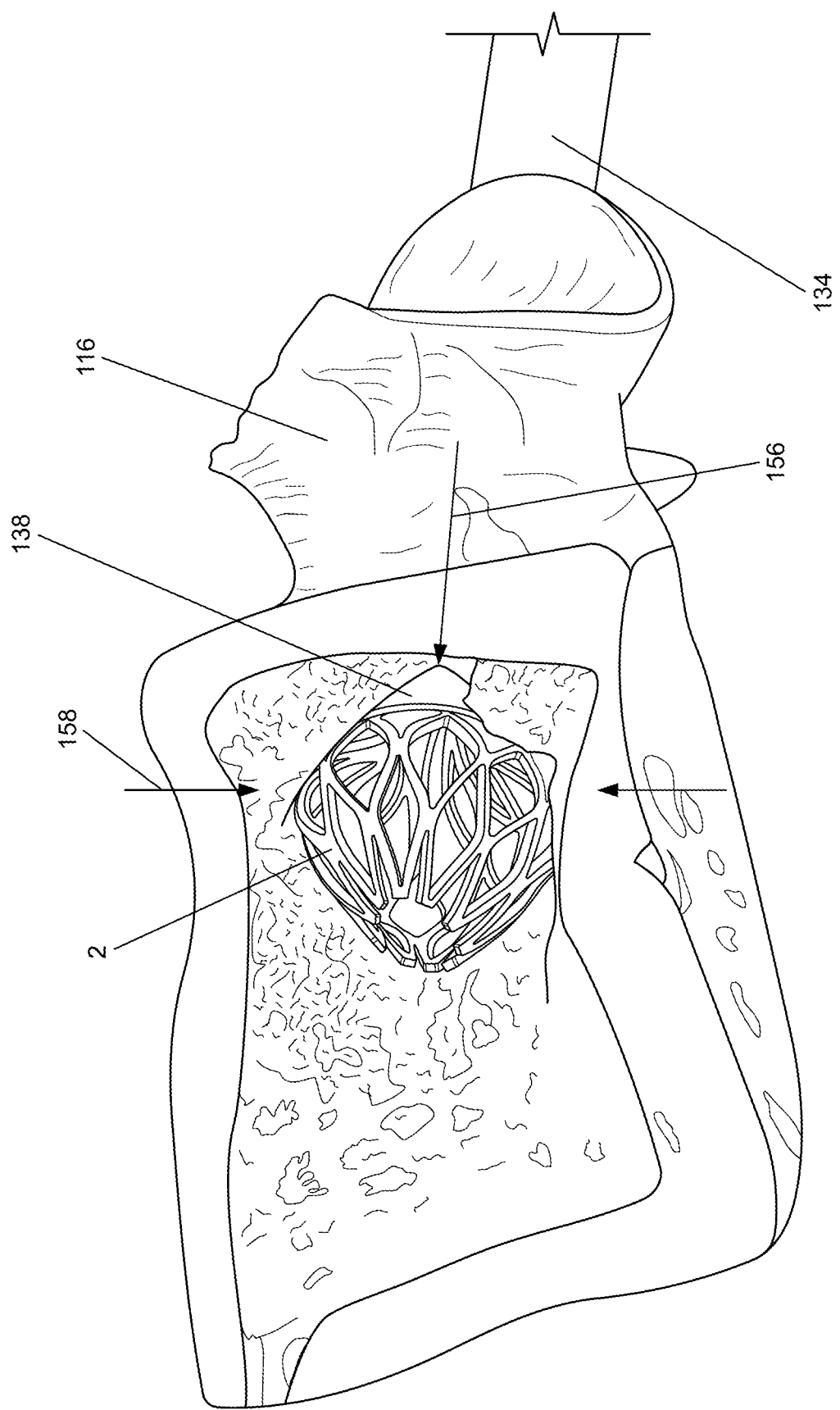
FIGS. 44 through 46 illustrate a variation of the method of retrieving the expandable support device.
Figure 45:
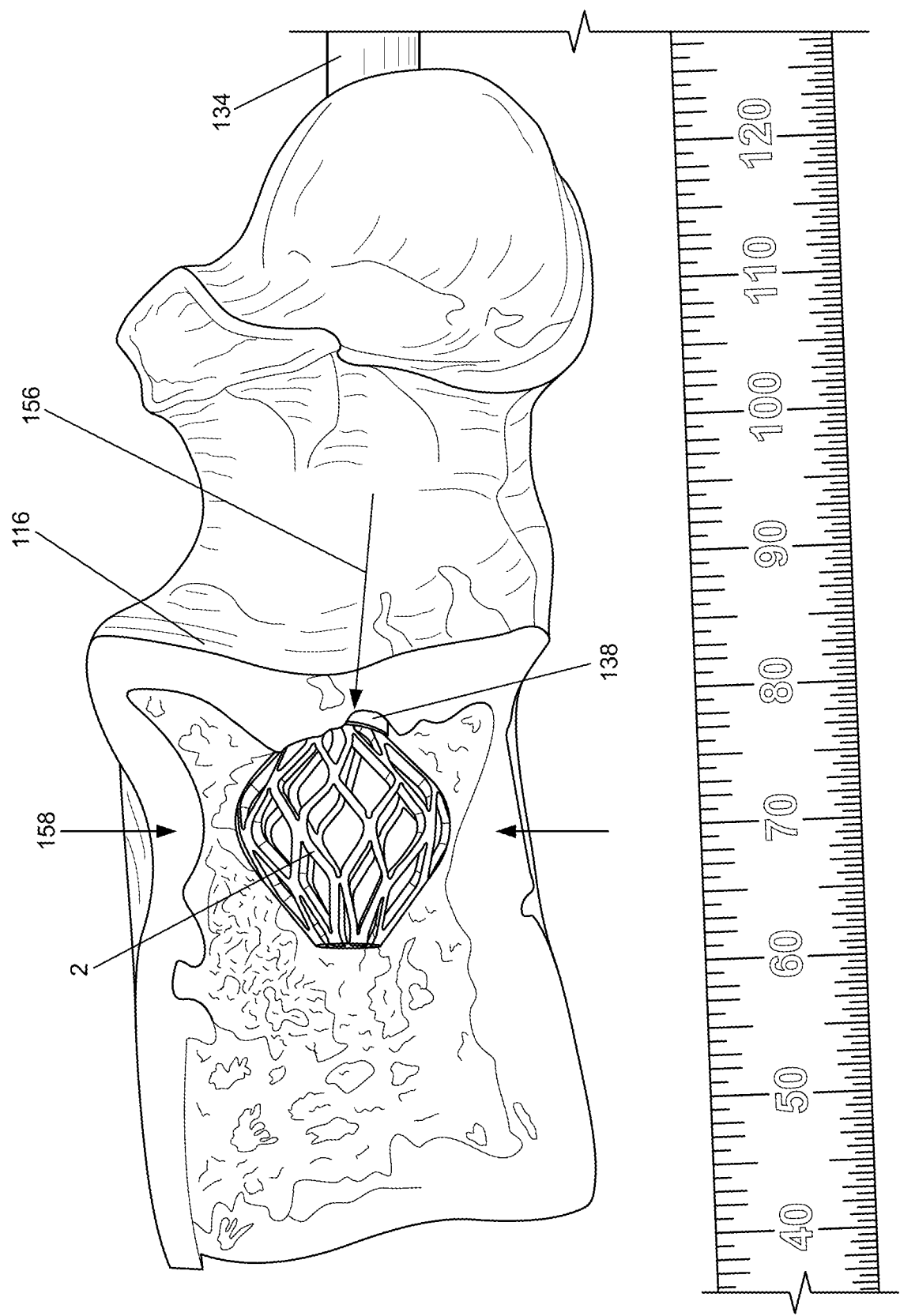

FIGS. 44 and 45 illustrate that the expandable support device 2 can be in a radially expanded configuration in the vertebra. The expandable support device 2 can be attached to the deployment tool 134 (e.g., never released during deployment or released and re-attached/re-engaged). The expandable support device 2 can be in an incorrect location, improperly radially expanded, or otherwise desirous of being removed, repositioned, or otherwise redeployed. The recovery sheath 138 can be translated, as shown by arrow 156, toward and onto the expandable support device 2. The expandable support device 2, substantially other than the recovery sheath 138, can be substantially stationary with respect to the expandable support device 2. The recovery sheath 138 can begin to radial compress, as shown by arrows 158, the expandable support device 2.

Figure 46:
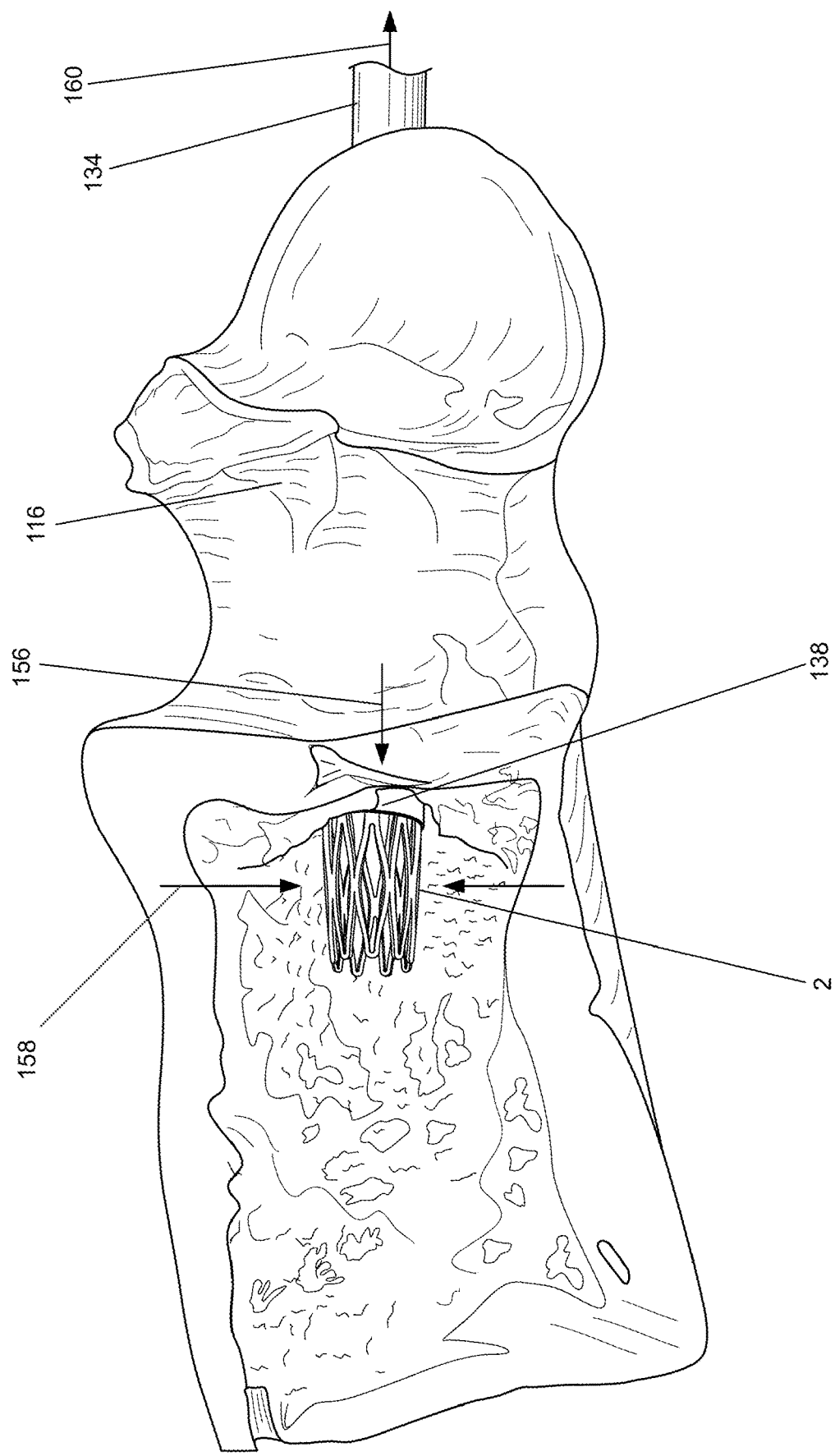

FIG. 46 illustrates that the recovery sheath 138 can be additionally translated, as shown by arrow 156, over the expandable support device 2. The expandable support device 2 can radially contract, as shown by arrows 158, for example into a substantially radially contracted configuration. The deployment tool 134 can then by translated, as shown by arrow 160, away from the vertebra 116. The deployment tool 134 can reposition the expandable support device 2 and retract the recovery sheath 138, and for example radially expand the expandable support device 2 in the vertebra 116 (e.g., with or without removing the expandable support device from the vertebra).

Figure 47:
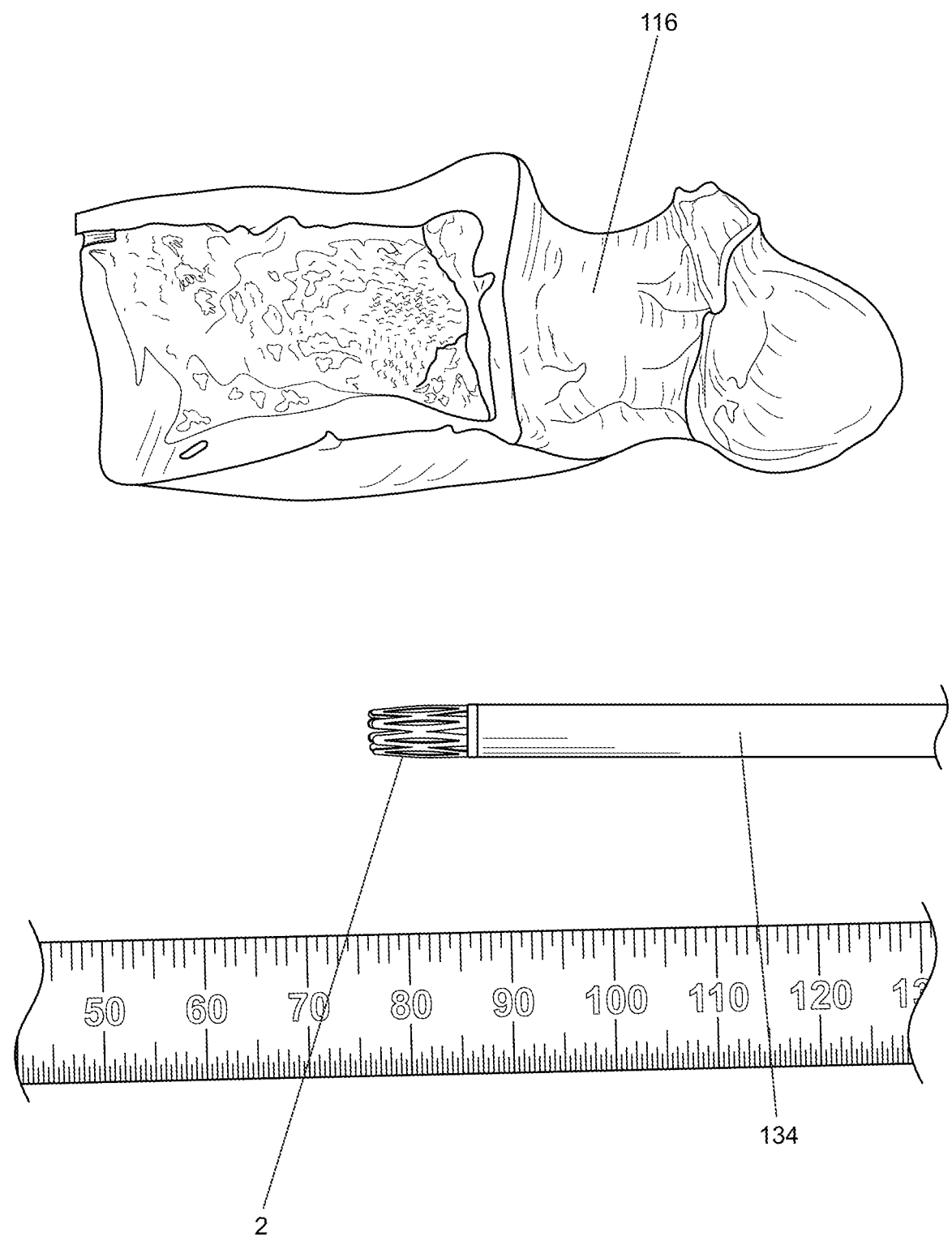
FIG. 47 illustrates a variation of the deployment tool with the expandable support device removed from the vertebra.

FIG. 47 illustrates that the deployment tool 134 can completely remove the expandable support device 2 from the vertebra 116. The same or a different expandable support device 2 can then be deployed into the vertebra 116.

Figure 48:
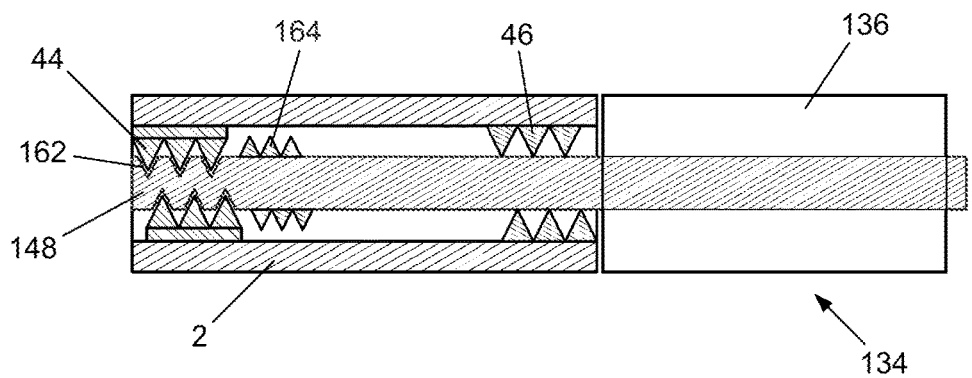
FIGS. 48 through 52 illustrate longitudinal cross-sectional views (similar to sectional view D-D) of a variation for the deployment and recovery of a variation of the expandable support device.

FIG. 48 illustrates that the expandable support device 2 can be releasably attached to the deployment tool 134. The deployment tool 134 can have the deployment rod 148 extending from the deployment rod sheath 136. The deployment tool 148 can have distal rod threads 162. The distal rod threads 162 can be releasably (e.g., rotatably) attached to the distal device threads 44. The deployment rod 148 can have proximal rod threads 164 between the distal rod threads 162 and the proximal device threads 46. The deployment tool 134 can have a deployment rod sheath 136. The deployment rod sheath 136 can abut, interference fit or otherwise attach to the proximal end of the expandable support device 2.

Figure 49:
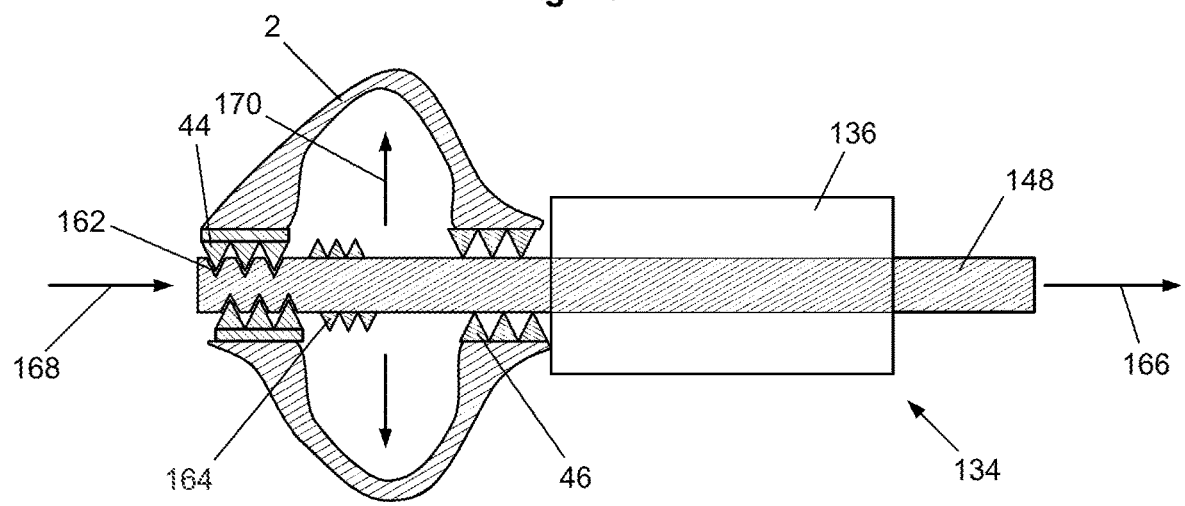

FIG. 49 illustrates that the deployment rod 148 can be forcibly proximally translated, as shown by arrow 166. The expandable support device 2 can then be longitudinally compressed, as shown by arrow 168, between the distal device threads 44 and the deployment rod sheath 136 and/or other proximal attachment device (not shown). The expandable support device 2 can radially expand, as shown by arrows 170, for example due to the longitudinal compression 152.

Figure 50:
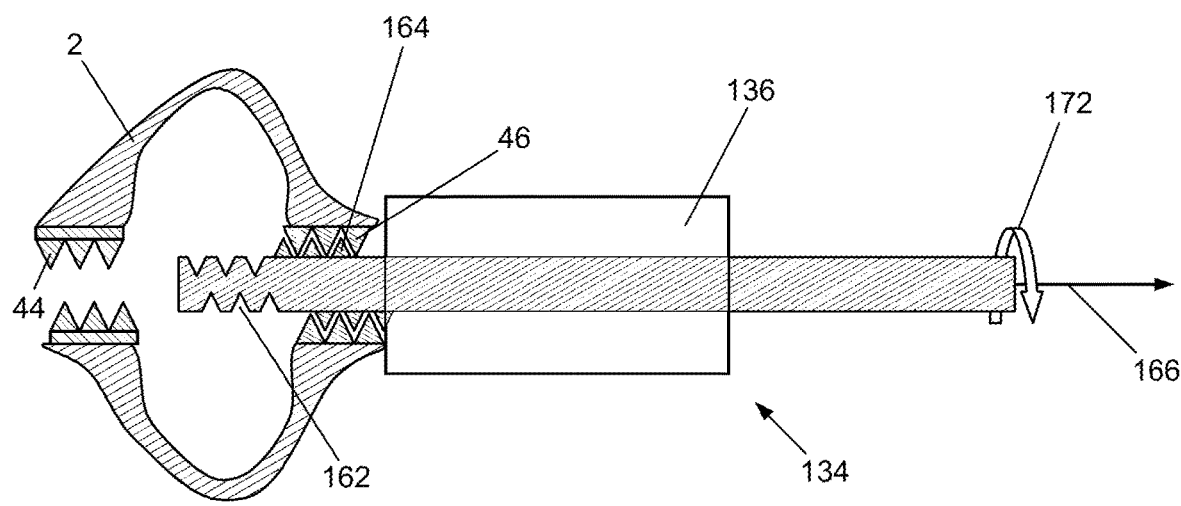

FIG. 50 illustrates that, with the expandable support device 2 in a radially expanded configuration, the deployment rod 148 can be proximally translated, as shown by arrow 166. The translation of the deployment rod can, for example, be due to rotation of the deployment rod 148, as shown by arrow 172, and the threading of distal rod threads 162 through the distal device threads 44.

The proximal rod threads 164 can thread into the proximal device threads 46. If the placement and configuration of the expandable support device 2 is satisfactory, the proximal rod threads 164 can be rotatably removed from the proximal device threads 46. The deployment device can then be removed entirely. If the placement and configuration of the expandable support device 2 is not satisfactory, the expandable support device 2 can be radially contracted and removed from the treatment site, as described infra.

Figure 51:
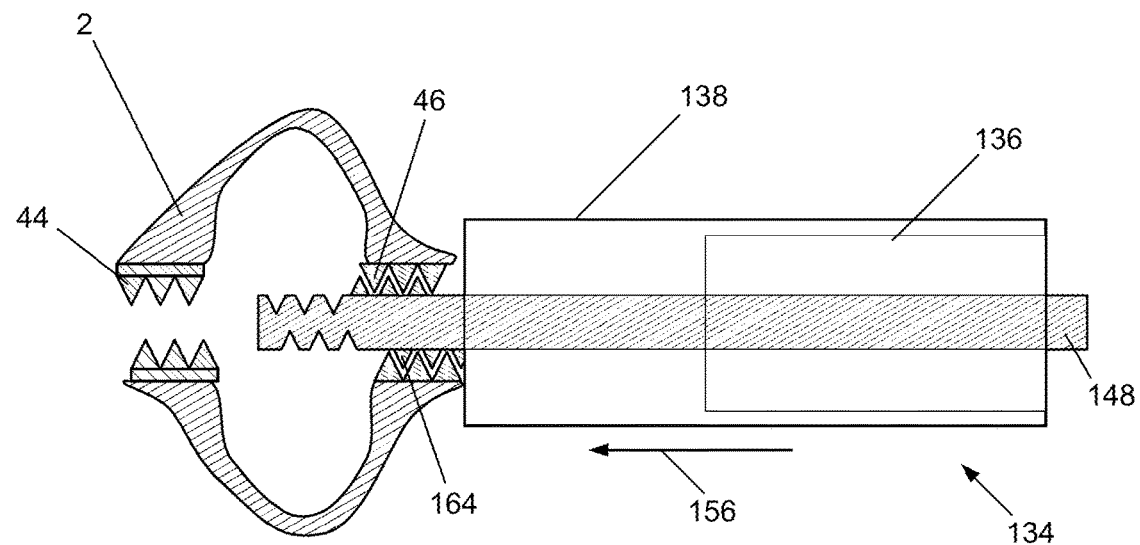

FIG. 51 illustrates that the recovery sheath 138 can be translated, as shown by arrow 156, toward the expandable support device 2, and/or the expandable support device 2 can be translated (e.g., via translation of the attached deployment rod 148) toward the recovery sheath 138.

Figure 52:
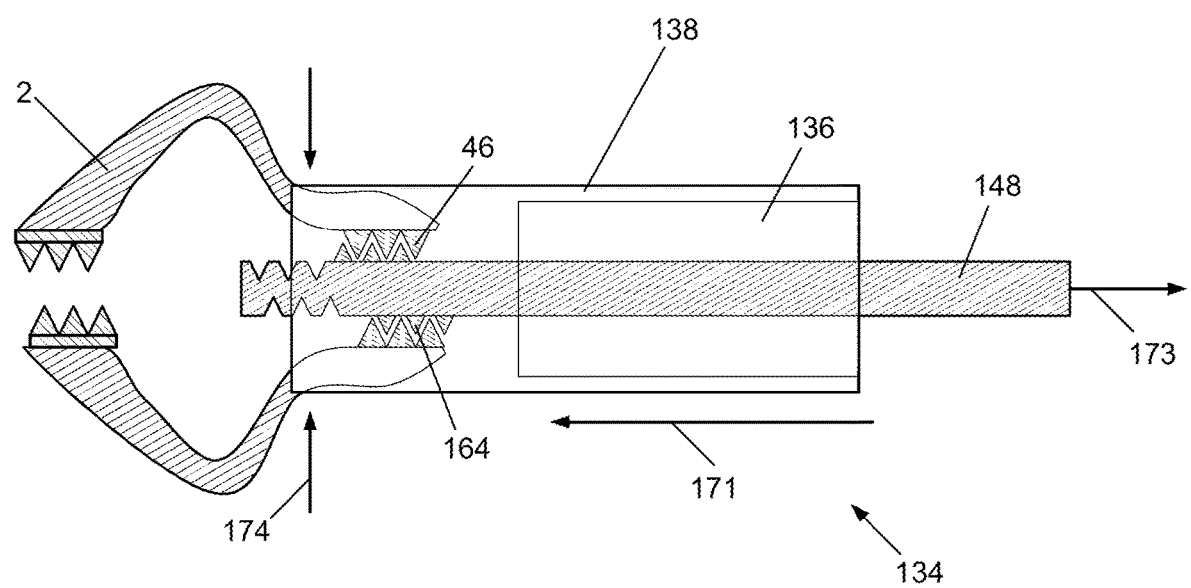

FIG. 52 illustrates that the recovery sheath 138 can be translated onto the expandable support device 2, as shown by arrow 171, and/or the expandable support device 2 (e.g., via translation of the attached deployment rod 148) can be translated, as shown by arrow 173, into the recovery sheath 138 and/or the expandable support device 2 can be translated toward the recovery sheath 138. As the expandable support device 2 is translated into the recovery sheath 138, the expandable support device 2 can be radially contracted, as shown by arrows 174. When the expandable support device 2 is sufficiently radially contracted 174 and/or in the recovery sheath 138, the deployment tool 134 and the expandable support device 2 can be removed from the treatment site.

Figure 53:
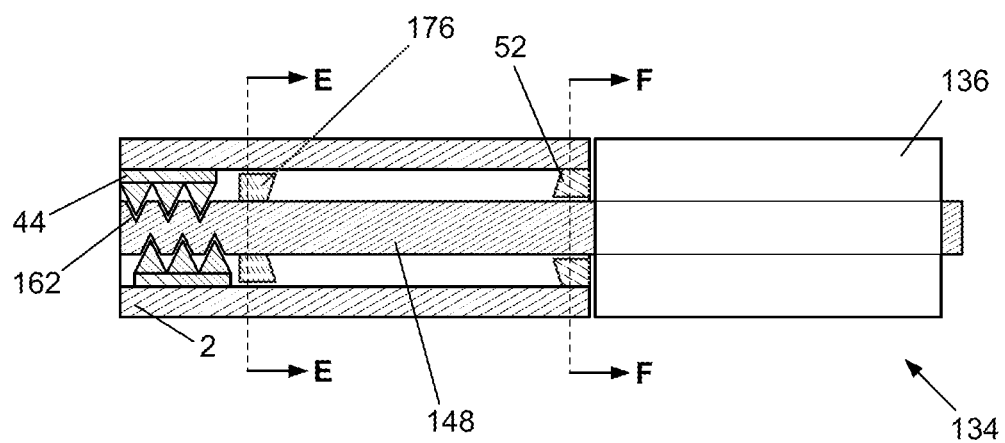
FIG. 53 illustrates a variation of the expandable support device loaded on a variation of the deployment tool.
Figure 54:
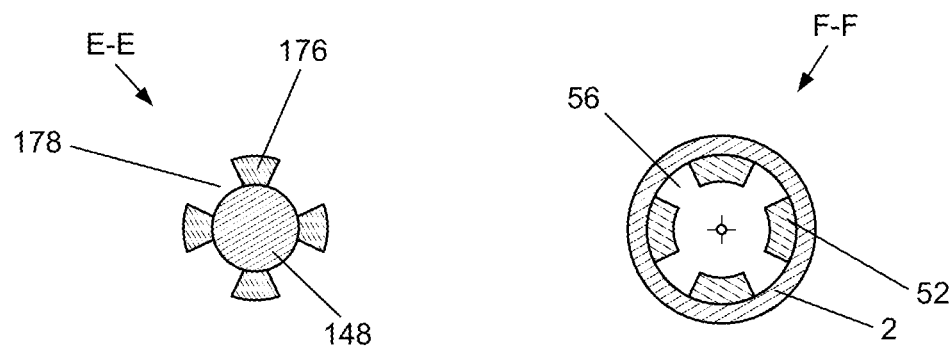
FIG. 54 illustrate cross-sections E-E and F-F of the deployment rod and expandable support device, respectively, of FIG. 53 in aligned unlocked configurations.
Figure 55:
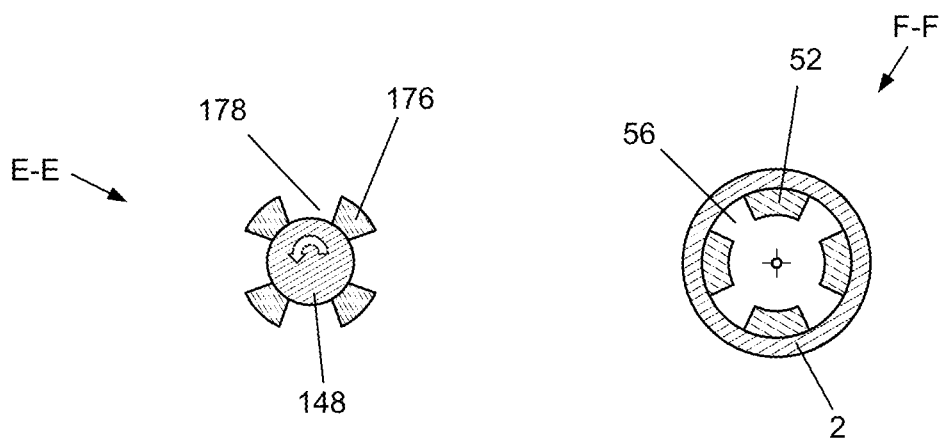
FIG. 55 illustrate cross-sections E-E and F-F of the deployment rod and expandable support device, respectively, of FIG. 53 in aligned locked configurations.
Figure 58:
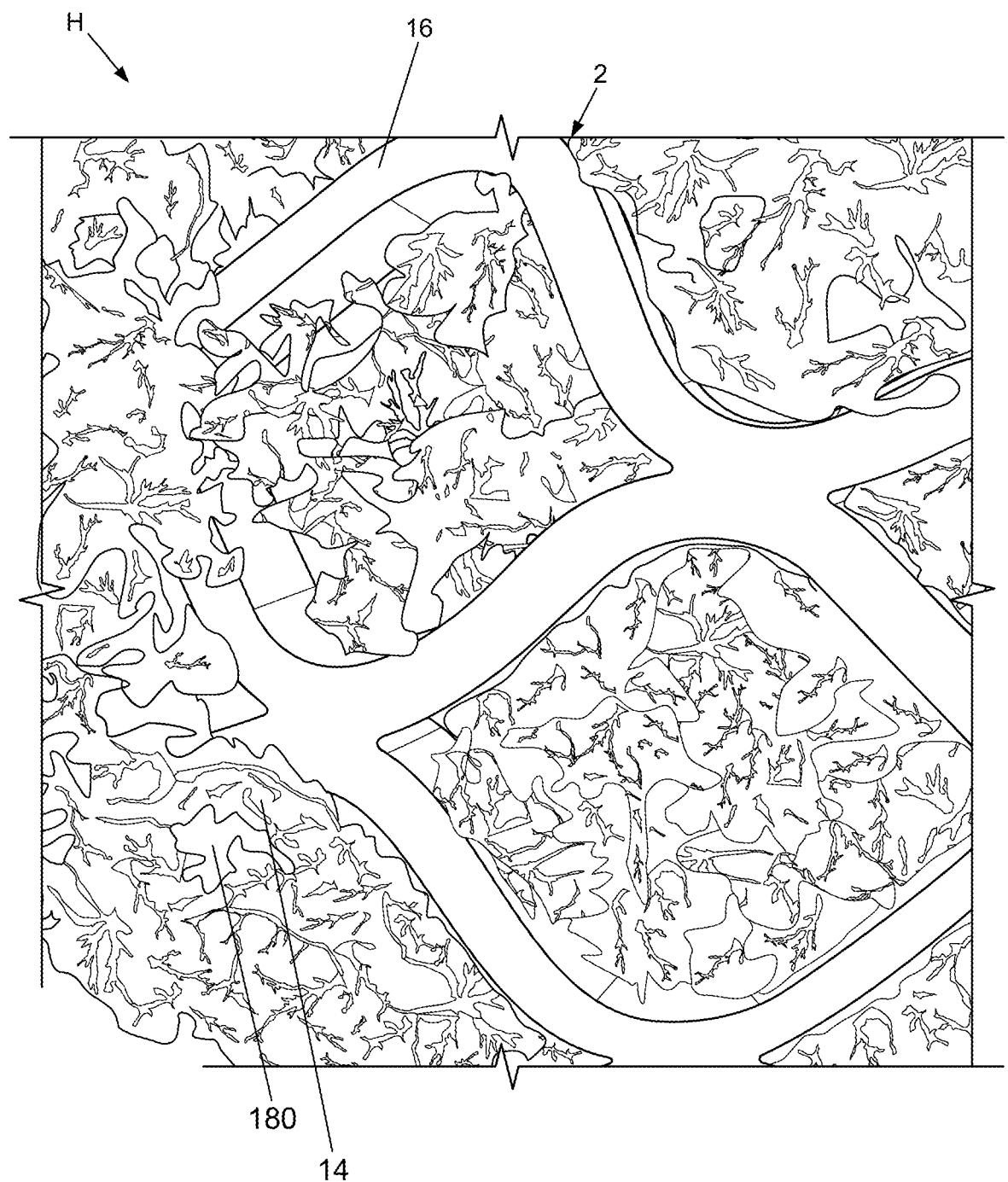
FIG. 58 is a close-up view of section H of FIG. 56.

FIGS. 53 and 54 illustrates that the deployment tool 134 can have a deployment rod key 176. The deployment rod key 176 can be configured to interference fit against the device key 52 when the expandable support device 2 and the deployment tool 134 are in a locked configuration, as shown in FIG. 54. As shown in FIG. 55, when the deployment rod 148 is rotated into an unlocked configuration, as shown by arrow, the deployment rod key 176 can be configured to translate through the device key port 56, and the device key 52 can translate through the deployment rod key port 178.

After being radially expanded, the expandable deployment device 2 can be detached from the deployment tool 134 by turning the deployment rod 148 to the unlocked configuration, and then proximally translating the deployment rod 148. The expandable support device 2 can be radially contracted into the recovery sheath 138 by turning the deployment rod 148 to the locked configuration, and then distally translating the recovery sheath 138 while holding and/or proximally translating the deployment rod 148.

FIGS. 56 though 58 illustrate an expandable support device 2 explanted from a bone 180 can have bone substantially surrounding the struts 16. The bone 180 can pass through the pores 14. The struts 16 and joints 18 can be forced through the bone 180 during deployment of the expandable support device 2 in the bone 180. The bone 180 can grow around the struts 16 and joints 18 after deployment.

Figure 59:
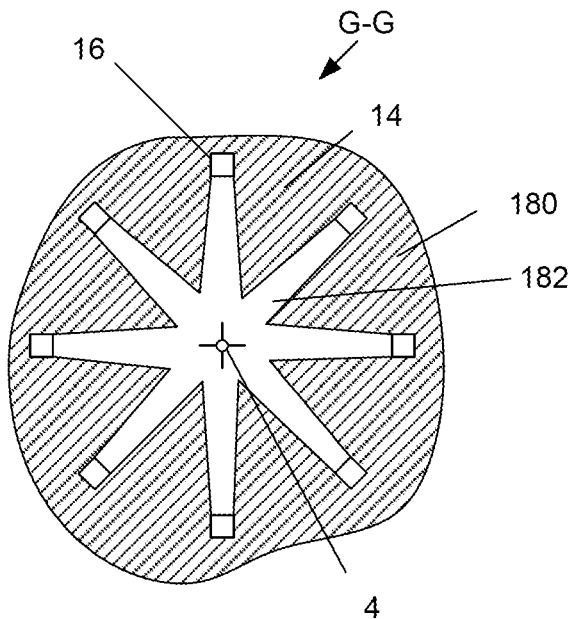
FIGS. 59 through 61 illustrate various variations of cross-section G-G of FIG. 57.

FIG. 59 illustrates the struts 16 can deploy through the bone 180. When the struts 16 expand (e.g., during radial expansion of the expandable support device 170), the struts 16 can create voids or struts tracks 182. The struts 16 can have a wide enough dimension transverse to the direction of radial expansion that the strut tracks 182 can be large enough to access and fill partially or completely with any material (e.g., BMP, bone cement, morselized bone, bone growth matrix). The struck tracks 182 can also be filled partially or completely with the threads or longitudinal vanes 96.

Figure 60:
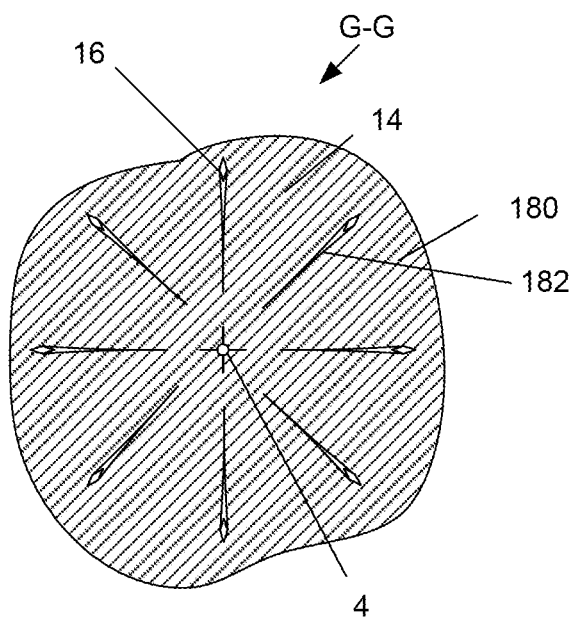

FIG. 60 illustrates that the strut 16 can be configured to leave a large or small strut track 182 during radial expansion of the expandable support device 170. The width of the track 182 can correspond to the strut width. The struts 16 can have a narrow dimension transverse to the direction of radial expansion. For example, the strut 16 can have a diamond-shaped cross-section with a longer dimension in the radial dimension than the angular dimension (i.e., the strut dimension transverse to the radial dimension). The visco-elastic nature of bone (e.g., cancellous bone and/or cortical bone) can cause the bone to back-fill the tracks 182 as shown in FIG. 60.

Figure 61:
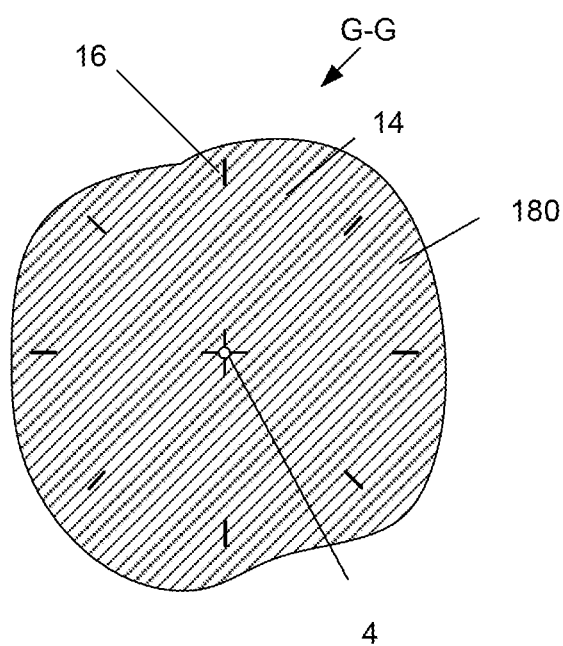

FIG. 61 illustrates that the strut 16 can be configured to leave a nominal or no strut track during radial expansion of the expandable support device 170. The struts 16 can have a nominal or otherwise substantially no thickness in the angular dimension (i.e., the strut dimension transverse to the radial dimension).

The expandable support device 2 can also be used for various other medical and non-medical applications: to immobilize and/or stabilize orthopedic trauma, hip fractures and other trauma, clavicle fractures and other trauma, small bones (e.g., carpals, tarsals, talus, other hand, feet and ankle bones) fractures and other trauma, other long bone repair (e.g., internal bone splinting), spinal fusion, use as an intermedullary canal implant to anchor an artificial joint, use as a bone anchor for a tendon repair or ligament implant (e.g., for anterior cruciate ligament repair or replacement), or combinations thereof.

Any elements described herein as singular can be pluralized (i.e., anything described as "one" can be more than one). Any species element of a genus element can have the characteristics or elements of any other species element of that genus. The above-described configurations, elements or complete assemblies and methods and their elements for carrying out the invention, and variations of aspects of the invention can be combined and modified with each other in any combination. All devices, apparatuses, systems, and methods described herein can be used for medical (e.g., diagnostic, therapeutic or rehabilitative) or non-medical purposes.

We claim:

1. An expandable support device for repairing damaged bone, the expandable support device having a longitudinal axis, and comprising:
   a first terminal end comprising a radially external first attachment configuration;
   a second terminal end comprising a radially external second attachment configuration, and a radially internal attachment configuration;
   an expandable length comprising a first strut having a first strut first cross-section, and a second strut connected to the first strut;
   wherein the first strut is substantially deformable;
   wherein the first strut first cross-section is configured to encourage bone growth toward the longitudinal axis,
   wherein the device has a radially expanded configuration, wherein in the radially expanded configuration the longitudinal center of the device has a larger radius than the radius of the first terminal end, wherein the first strut is configured to be forced through bone when the device is radially expanded to the radially expanded configuration, wherein when the device is in a fully radially contracted configuration, the first strut first cross-section has a first side and a second side angled relative to the first side such that the first and second sides intersect to form a tip, wherein when the device is in the fully radially contracted configuration, the tip extends from a first end of the first strut to a second end of the first strut, wherein when the device is in the fully radially contracted configuration, a straight axis perpendicular to the longitudinal axis intersects the longitudinal axis, an apex of the tip, and a surface of the first strut opposite the apex of the tip, wherein the first strut further comprises a first strut second cross-section, wherein the first strut first cross-section is perpendicular to the longitudinal axis, wherein the first strut second cross-section is parallel to the first strut first cross-section, wherein when the device is in the fully radially contracted configuration, the first strut has a first thickness as measured between a radial innermost surface of the first strut cross-section and the apex of the tip of the first strut first cross-section, wherein when the device is in the fully radially contracted configuration, the first strut has a second thickness as measured between a radial innermost surface of the first strut cross-section and a radial outermost surface of the first strut second cross-section, and wherein the first thickness is greater than the second thickness.

2. The device of claim 1, further comprising a bone growth material, wherein the first strut has an extension, and wherein when the device is in a fully radially expanded configuration, and the extension extends away from the first strut and the tip.

3. The device of claim 2, wherein the first strut comprises the bone growth material.

4. The device of claim 2, wherein the first strut is coated with the bone growth material.

5. The device of claim 4, wherein the bone growth material circumferentially surrounds the first strut first cross-section.

6. The device of claim 4, wherein the first strut has a first strut first side closer to the longitudinal axis and a first strut second side farther from the longitudinal axis than the first strut first side, and wherein the bone growth material is on the first strut first side.

7. The device of claim 6, wherein the first strut second side is not substantially coated with the bone growth material.

8. The device of claim 1, wherein the first strut first cross-section comprises a needle tip, wherein the first strut comprises an extension, and wherein when the device is in a fully radially expanded configuration, the extension extends away from the first strut and the tip.

9. The device of claim 1, wherein the first strut first cross-section comprises a chisel tip.

10. The device of claim 1, wherein the first strut comprises a longitudinal vane.

11. The device of claim 1, further comprising:
    a detachable deployment rod comprising an expandable support device engager; and
    a detachable retrieval sheath translatably slidable with respect to the deployment rod, wherein the retrieval sheath is configured to radially compress the expandable support device.

12. The device of claim 1, wherein the first strut first cross-section is small enough to allow the bone to substantially back-fill track voids created by radial expansion of the first strut first cross-section.

13. The device of claim 12, wherein a second strut cross-section is small enough to allow the bone to substantially back-fill track voids created by radial expansion of the second strut cross-section.

14. The device of claim 1, further comprising a detachable deployment element configured to attach to the first terminal end, wherein the first strut is exposed when the detachable deployment element is attached to the first terminal end.

15. The device of claim 1, wherein the apex of the tip points away from the longitudinal axis.

16. The device of claim 8, wherein the needle tip has a first needle side and a second needle side, and wherein the needle tip has a needle tip angle from about 0.5 degrees to about 25 degrees.

17. An expandable support device for repairing damaged bone, the expandable support device having a longitudinal axis, and comprising:
- a first terminal end comprising a radially external first attachment configuration;
- a second terminal end comprising a radially external second attachment configuration, and a radially internal attachment configuration;
- a first strut having a first strut first cross-section and an extension;
- a second strut connected to the first strut;
- wherein the first strut is substantially deformable;
- wherein the first strut first cross-section is configured to encourage bone growth toward the longitudinal axis;
- wherein the device has a radially expanded configuration, wherein in the radially expanded configuration the longitudinal center of the device has a larger radius than the radius of the first terminal end, wherein the first strut is configured to be forced through bone when the device is radially expanded to the radially expanded configuration and wherein when the device is in a fully radially expanded configuration, the extension extends from the first strut into a fillable space; and
- wherein when the device is in a fully radially contracted configuration, an outer diameter of the second terminal end is less than an outer diameter of the longitudinal center of the device.

18. The device of claim 17, further comprising a detachable deployment element configured to attach to the first terminal end, wherein the first strut is exposed when the detachable deployment element is attached to the first terminal end.

19. The device of claim 17, further comprising a bone growth material.

20. The device of claim 17, wherein the first strut further comprises a first strut second cross-section, wherein the first strut first cross-section is perpendicular to the longitudinal axis, wherein the first strut second cross-section is parallel to the first strut first cross-section, wherein when the device is in the fully radially contracted configuration, the first strut first cross-section has a different shape than the first strut second cross-section, wherein the first strut cross-section has an apex that points away from the longitudinal axis, and wherein the apex extends along a length of the first strut.

21. The device of claim 17, wherein the first strut first cross-section has a first side and a second side angled relative to the first side such that the first and second sides intersect to form a strut tip, wherein the strut tip extends along a length of the first strut, and wherein the strut tip is a radial outer-most point of the first strut.

22. The device of claim 21, wherein the first strut first cross-section has a portion that becomes thinner as the radial distance from the longitudinal axis increases.

23. The device of claim 21, wherein the first strut first cross-section has a strut dimension measured along a portion of a circumference of the device, and wherein the strut dimension decreases as the radial distance from the longitudinal axis increases.

24. The device of claim 17, wherein when the device is in the fully radially contracted configuration, the first strut first cross-section has a first side and a second side angled relative to the first side such that the first and second sides intersect to form a tip, and wherein when the device is in the fully radially contracted configuration, an expandable section of the device has a cylindrical lumen with a constant diameter.

25. An expandable support device for repairing damaged bone, the expandable support device having a longitudinal axis, and comprising:
- a unitary body comprising internal threads;
- a first terminal end comprising a radially external first attachment configuration;
- a second terminal end comprising a radially external second attachment configuration, and a radially internal attachment configuration;
- a first strut having a first strut transverse cross-section;
- a second strut connected to the first strut;
- a detachable deployment element configured to attach to the first terminal end; and
- wherein the first strut is substantially deformable, wherein the first strut transverse cross-section is configured to encourage bone growth toward the longitudinal axis, wherein the first strut is exposed when the detachable deployment element is attached to the first terminal end, wherein the first strut is configured to be forced through bone when the device is radially expanded to a radially expanded configuration, wherein when the device is in a fully radially contracted configuration, the first strut transverse cross-section has a first side and a second side angled relative to the first side such that the first and second sides intersect to form a tip, and wherein when the device is in the fully radially contracted configuration, the tip is at a middle region of the first strut.

26. The device of claim 25, wherein the first strut transverse cross-section has at least one radial outer most side, and wherein a line normal to the at least one radial outer-most side does not intersect the longitudinal axis.

27. The device of claim 25, wherein the first strut transverse cross-section has at least one radial outer most side, and wherein a line normal to the at least one radial outer-most side intersects the longitudinal axis.

* * * * *